(12) United States Patent
D'Aniello et al.

(10) Patent No.: US 11,524,031 B2
(45) Date of Patent: Dec. 13, 2022

(54) USE OF A COMBINATION OF D-ASPARTIC AND L-ASPARTIC ACIDS OR SALTS THEREOF FOR THE TREATMENT OF MALE INFERTILITY

(71) Applicant: MERCK SERONO S.p.A., Rome (IT)

(72) Inventors: Salvatore D'Aniello, S. Antimo (IT); Enrico D'Aniello, S. Antimo (IT)

(73) Assignee: MERCK SERONO S.P.A., Rome (IT)

( * ) Notice: Subject to any disclaimer, the term of this patent is extended or adjusted under 35 U.S.C. 154(b) by 0 days.

(21) Appl. No.: 16/504,372

(22) Filed: Jul. 8, 2019

(65) Prior Publication Data

US 2019/0328778 A1 Oct. 31, 2019

Related U.S. Application Data

(60) Continuation of application No. 14/288,439, filed on May 28, 2014, now Pat. No. 10,342,826, which is a division of application No. 13/320,780, filed as application No. PCT/IT2010/000222 on May 19, 2010.

(30) Foreign Application Priority Data

May 19, 2009 (IT) .............................. RM2009A0253

(51) Int. Cl.
| | | |
|---|---|---|
| *A61K 33/30* | (2006.01) | |
| *A61K 45/06* | (2006.01) | |
| *A61K 31/122* | (2006.01) | |
| *A61K 31/198* | (2006.01) | |
| *A61K 31/519* | (2006.01) | |

(52) U.S. Cl.
CPC ............ *A61K 33/30* (2013.01); *A61K 31/122* (2013.01); *A61K 31/198* (2013.01); *A61K 31/519* (2013.01); *A61K 45/06* (2013.01)

(58) Field of Classification Search
CPC .. A61K 31/122; A61K 31/198; A61K 31/519; A61K 33/30; A61K 45/06
See application file for complete search history.

(56) References Cited

U.S. PATENT DOCUMENTS

| | | | |
|---|---|---|---|
| 4,804,674 A | | 2/1989 | Curtis-Prior et al. |
| 5,397,786 A | * | 3/1995 | Simone ..................... A23L 2/52 514/300 |
| 5,863,940 A | | 1/1999 | Cavazza |
| 8,202,908 B1 | | 6/2012 | Arnold |
| 10,342,826 B2 | | 7/2019 | D'Aniello et al. |
| 2003/0096794 A1 | | 5/2003 | Niehoff |
| 2006/0210692 A1 | * | 9/2006 | Mower ..................... A61K 8/29 426/618 |

FOREIGN PATENT DOCUMENTS

| | | |
|---|---|---|
| EP | 0 242 980 | 10/1987 |
| EP | 1848416 | 10/2007 |
| IT | 1359913 | 3/2007 |
| JP | 62-234017 | 10/1987 |
| WO | WO 2005/120488 | 12/2005 |

OTHER PUBLICATIONS

Zhong et al, Nutrition 2002;18:872-879.*
Wolinsky, Sports Nutrition: vitamins and trace elements, 1997.*
D'Aniello, G. et al. "Occurrence of D-aspartic acid in human seminal plasma and spermatozoa: Possible role in reproduction" *Fertility and Sterility*, Nov. 1, 2005, pp. 1444-1449, vol. 84, No. 5.
De Aloysio, D. et al. "The Clinical Use of Arginine Aspartate in Male Infertility" *ACTA Europaea Fertiliatis*, Sep. 1982, pp. 133-167, vol. 13, No. 3.
Koyuncuoglu, H, et al. "Antagonistic Effect of L-aspartic Acid on Decrease in Body Weight, and Food and Fluid Intake, and Naloxone Reversible Rectal Temperature Depression Caused by D-aspartic Acid" *Polish Journal of Pharmacology and Pharmacy*, Jan. 1, 1982, pp. 333-337, vol. 34, No. 5-6.
Sinisi, A. et al. "Homozygous mutation in the prokineticin-receptor2 gene (Val274Asp) presenting as reversible Kallmann syndrome and persistent oligozoospermia: Case Report" *Human Reproduction*, Oct. 2008, pp. 2380-2384, vol. 23, No. 10.
D'Aniello, G. et al. "Reproductive implication of D-aspartic acid in human pre-ovulatory follicular fluid" *Human Reproduction*, Dec. 2007, pp. 3178-3183, vol. 22, No. 12.
Written Opinion in International Application No. PCT/IT2010/000222, dated Sep. 2, 2010, pp. 1-5.
Fang, Y.-Z. et al. "Free Radicals, Antioxidants, and Nutrition" *Nutrition*, 2002, pp. 872-879, vol. 18, No. 10.
Wolinsky, I. "Sports Nutrition: Vitamins and Trace Elements" 1997, pp. 1-3.
Oh, S. I. et al. "Aspartate modulates the ethanol-induced oxidative stress and glutathione utilizing enzymes in rat testes" *Experimental and Molecular Medicine*, Mar. 2002, pp. 47-52, vol. 34, No. 1.
Ghelberg, N. W. et al. "Lead-Induced Experimental Lesions of the Testis and Their Treatment" *Journal of Applied Toxicology*, 1981, pp. 284-286, vol. 1, No. 5.
Krishnamurthy, H. et al. "Radioprotective effect of zinc aspartate on mouse spermatogenesis: a flow cytometric evaluation" *Mutation Research*, 1998, pp. 111-120, vol. 401.
University of Chicago, Copyright 2005, pp. 1-2.
WebMD, 2004, pp. 1-2.
WebMD, 2002, pp. 1-2.
D'Aniello et al. (IT1359913), accessible to the public on Mar. 15, 2007, p. 1.

* cited by examiner

*Primary Examiner* — Jean P Cornet
(74) *Attorney, Agent, or Firm* — Saliwanchik, Lloyd & Eisenschenk

(57) ABSTRACT

The present invention concerns the use of a combination consisting of D-aspartic and L-aspartic acids or L-aspartic acid used alone to stimulate the procreative activity in the man by increment of spermatozoon number and motility.

11 Claims, 3 Drawing Sheets

Figure 1:
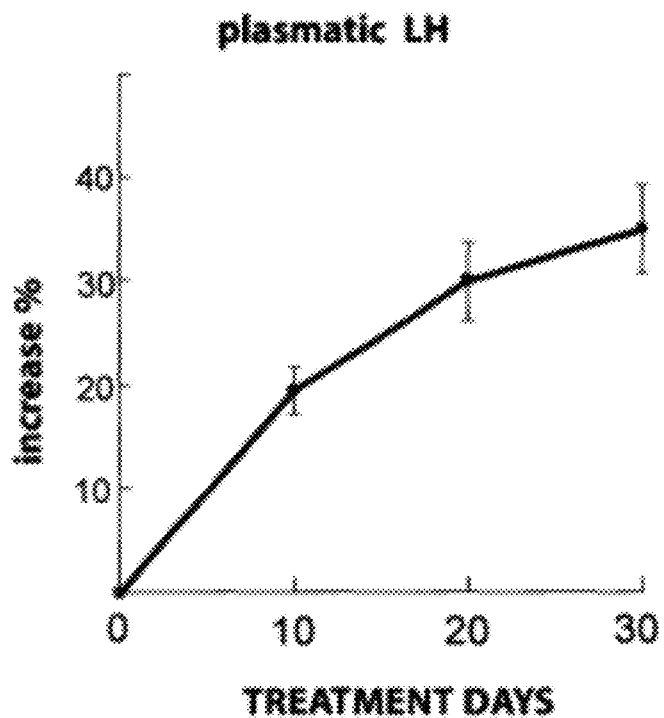

USE OF A COMBINATION OF D-ASPARTIC AND L-ASPARTIC ACIDS OR SALTS THEREOF FOR THE TREATMENT OF MALE INFERTILITY

CROSS-REFERENCE TO RELATED APPLICATIONS

This application is continuation of U.S. Ser. No. 14/288,439, filed May 28, 2014, now U.S. Pat. No. 10,342,826, which is a divisional of U.S. Ser. No. 13/320,780, filed Dec. 22, 2011, abandoned, which is the U.S. national stage application of International Patent Application No. PCT/IT2010/000222, filed May 19, 2010.

The present invention concerns the use of a combination of D-aspartic and L-aspartic acids or salts thereof for the treatment of male infertility. In particular, the invention concerns the use of a mixture consisting of a mixture of D-aspartic and L-aspartic acids or salts thereof, preferably at least at ratio 1:1 in order to stimulate the man procreative activity by means of an increment of spermatozoon number and motility.

The male infertility can be caused by disorders relating to spermatozoon production, emission or functionality and represents approximately 35% of couple infertility causes. It can be caused by possible past or presently occurring genitourinary infections; diseases like the varicella, measles or parotitis, viral disease that in men can result in orchitis (testicle infection); sexual transmission diseases; past surgeries or genital level traumas. Moreover, the life style, as the use of alcohol, smoke, drugs and hazardous works and environmental factors can play an important role. Varicocele can result in active spermatozoon generation deficit. Also FSH (follitropin), LH (luteotropin), PRL (prolactin) and T (testosterone) altered levels can affect the process of spermatozoon production.

Currently used treatments for male infertility involve the use of injected or oral administered drugs. Among injected drugs, Menotropin, active principle in menogon vials, comprising a preparation of gonadotropines (FSH and LH, in equal amount) extracted from post-menopause woman urine, therefore named menopause human hormone (HMG), is used. HMG acts directly on ovaries and testicles, by stimulating the ovulation process, spermatogenesis and steroidogenesis. Within testicles, FSH is essentially involved in stimulation of Sertoli cell maturation and affects moreover the maturation of seminipher tubules and the development of the spermatozoa. Since high androgen concentration is necessary in testicles, this can be obtained with a pre-treatment with HCG or according to the therapeutic scheme involving the combination with HCG 5000 UI weekly over 3 months. However, this therapy displays some disadvantages, for example HCG is not effective if orally administered and must be administered intramuscularly. In some cases anti-HCG antibody formation can be taken place as a result of a cyclical repeated administration of the product, thus resulting in an ineffective therapy. A further disadvantage of this therapy is high cost, since most used therapy scheme involves the intramuscular administration three times a week over a three month cycle and low patient compliance due to the repeated intramuscular weekly administrations.

An alternative therapy involves the treatment with gonadotropine (GnRH) releasing hormone. This therapy involves a pulsed administration using portable pump (intravenously or subcutaneously) at 90-120 minute intervals. Although such a treatment within three months restores the concentrations of testosterone and gonadotropines and stimulates the spermatogenesis, on the other hand it implies that the patient must carries a portable pump equipped with urinary catheter and this can be uncomfortable for these patients.

As to oral therapies, the same can comprise antiestrogens. These compounds (clomifen citrate and tamoxifene) have been widely used for the treatment of male infertility, in the absence of endocrine pathologies. Antiestrogens maintain ability to bind competitively estrogen receptors, both at hypothalamic and peripheral level, thus inducing an increase of gonadotropine plasma levels and secondarily intratesticular testosterone. The pharmacological effect on spermatogenesis would have to be exerted through the concentration increase of these hormones acting directly on the spermatogenesis. In particular clomifen citrate at low dosages (25-50 mg) administered for a 3-5 month is suitable to improve the semen characteristics, while higher concentrations (200-400 mg) induce a spermatogenesis suppression and reduction of sperm concentration.

Various not controlled studies have reported variable increments of sperm concentration and a pregnancy rate variable from 0 to 80% and wherein the treatment response was observed nearly exclusively for low to moderate oligozoospermia (10-20 milioni/ml) suffering patients. In the light of said data, the World Health Organization (WHO) carried out a double blind multicentre study, placebo versus clomifen citrate, for idiopathic oligozoospermia suffering patients which study detected no improvement of the rate pregnancy in patients treated with this drug (WHO, Special Programme of Research, Development and Research Training in Human Reproduction Annual Technical Report 1990. Geneva: WHO 1991: 146-7).

Again as an oral therapy, aromatase inhibitors, as for example testolactone, can be used. In not controlled studies, the administration of testolactone (1 g/day) to oligozoospermia suffering subjects has been suitable to increase the sperm concentration and pregnancy percent. In a successive random, placebo-controlled and double blind trial, with more elevated testolactone doses (2 g/day), no variation of semen parameters has been detected and no pregnancy has been observed for thus treated and placebo treated groups. Another compound displaying selective inhibitory activity on aromatase is anastrozole, that at 1 mg daily dose appears to be similar to testolactone for effects on spermatogenesis. Further studies are surely necessary in order to estimate the real effectiveness of these drugs for the treatment of male infertility due to extremely low number of subjects studied until today.

The administration of androgens represented one of the first therapeutic attempts carried out to improve seminal parameters in oligozoospermia affected patients. Currently two weak androgenic compounds are used. Mesterolon, a 5a-reduced testosterone derivative not affecting gonadotropine secretion has been used as mono therapy at daily concentrations from 50 to 150 mg in various trials resulting in different modifications of seminal parameters. The most recent studies and WHO analysis have not documented meaningful variations of all analyzed seminal parameters and pregnancy percentage compared to pre-treatment and placebo treated group values. Similarly testosterone undecanoate appeared to be suitable in improving seminal parameters in controlled studies without affecting gonadotropine and testosterone levels; however successive trials have not confirmed these results and therefore the use of this compound is to be further verified.

At last, L-arginine or other L-amino acid combinations and/or vitamin supplements as coadjuvants in oligoastenospermia and hyposomia, by oral administration 2-3 times daily for three months.

In the light of above it is apparent the need to provide new methods for the treatment of male infertility overcoming the disadvantages of the known methods.

D-aspartic acid is a natural amino acid detected firstly in 1977 by Antimo D'Aniello within octopus (marine mollusc scientifically named *Octopus vulgaris*) brain as published in collaboration with Antonio Giuditta in J. of Neurochemistry (Ref. 1-2). Successive researches carried out by the same author in collaboration with other Italian and not Italian researchers have demonstrated that the D-aspartic acid occurs not only in the nervous, but also in the endocrine system of many marine as mollusc, crustacean, opisthobranc and fish (Ref. 3-5) and terrestrial animals, as frog (Ref. 6-7), lucertola (Ref. 8), chicken (Ref. 9), rat (Ref. 9-11), sheep (12) and human (Ref. 13-15). The concentration is variable from species to species. Generally, in less advanced animals D-aspartic acid is present in a greater amount compared to more advanced ones. Moreover, it has been detected that this amino acid in mammals, including humans, during the embryonic life is found at elevated concentrations in brain where it plays a role in the development of nervous system. On the contrary, during the adult life, D-aspartic acid is present ad elevated concentrations in endocrine system and particularly in pituitary gland and testicle where it plays a role in the endocrine system. For a complete review see (Ref. 16) and following table 1, derived from a publication of the authors in *Brain Research Review* vol. 53, pages 215-234, 2006, showing the D-aspartate content in the nervous and endocrine tissues of several classes of animals.

TABLE 1

Table 1: Concentrations of the D-aspartic acid in various animal species tissues

| Species | Animals | Tissues | D-Aspartic acid nmol/g tissue |
|---|---|---|---|
| Molluscs | *Octopus vulgaris* | brain | 8000-15000 |
| | *Octopus vulgaris* | retina | 3000-4000 |
| | *Octopus vulgaris* | testicle | 2000-3000 |
| Opisthobrancs | *Aplysia fasciata* | ganglia | 600-800 |
| | *Aplysia limacina* | ganglia | 3000-4000 |
| Tunicates | *C. Intestinalis* | ganglia | 300-500 |
| Crustaceans | Rock lobster | brain | 4000-5000 |
| | Rock lobster | retina | 800-900 |
| Amphibians | *Rana esculenta* | testicle | 200-300 |
| | | Harder gland | 100-150 |
| Reptiles | *Podarcis sicula* | reproduction organs | 20-30 |
| Fishes | *Merlucius merlucius* | brain | 30-40 |
| Birds | *Gallus gallus* | | |
| | Embryo: | brain and retina | 300-600 |
| | Adult: | brain and retina | 30-50 |
| Mammal | Rat | brain (embryo) | 250-350 |
| | | brain (adult) | 15-30 |
| | | retina (neonatal) | 300-400 |
| | | retina (adult) | 30-60 |
| | | pituitary (2 day) | 10-20 |
| | | pituitary (adult) | 120-140 |
| | | pineal gland | 650-3000 |
| | | testicle (embryon) | 50-70 |
| | | testicle (adult) | 220-250 |
| | | liver | 10-20 |
| | Human | brain (embryon) | 340-380 |
| | | brain (adult) | 20-40 |

The values represent average concentration in nmol of D-Asp/g in fresh tissues (A. D'Aniello; *Brain Research Review*, 53, 215-234, 2006) (Ref. 16).

Studies about D-aspartic acid in rat have evidenced that, if this compound is orally administered, it is suitable to induce a temporary increase in blood of some hormones as: luteinizing hormone (LH) (Ref: 17-18), growth hormone (Ref: 18), prolactin (PRL) (Ref: 19) and testosterone (Ref: 17-18). Finally recently it has been also demonstrated that D-aspartic acid is involved in human male infertility (Ref. 20).

It has been observed for man that in seminal liquid and spermatozoa of physiologically fertile people (people who have number of spermatozoa higher than 20 millions/ml of seminal liquid and motility higher than 70%) D-aspartic acid is present at concentration of 80±24 nmol/ml in seminal liquid and 130±30 fmol/spermatozoon. Instead, in seminal liquid of infertile people, that is people who have a lower than normal number of spermatozoa in seminal liquid and a motility thereof under of physiological values (oligoastenozoospermia suffering) and in seminal liquid of people not having spermatozoa (azoospermia suffering), the content of the D-aspartic acid is meaningfully reduced both in seminal liquid and spermatozoa. Specifically, in seminal liquid of oligoastenozoospermia suffering subjects, D-aspartic acid is approximately 3 fold lower and in azoospermia suffering subjects is 6 fold lower. From 130±35 fmol/spermatozoon found in fertile to 60±10 fmol/spermatozoon values found in oligoastenozoospermia suffering people. Table 2 shows the content of D-aspartic acid in human seminal liquid and spermatozoa.

TABLE 2

Content of D-aspartic acid in human seminal liquid and spermatozoa

| (Seminal liquid) (nmol/ml) | | | Spermatozoa (fmol/spermatozoon) | |
|---|---|---|---|---|
| Normal[1] | OAT[2] | AZO[3] | Normal[1] | OAT[2] |
| 80 ± 10 | 26 ± 6.0 | 12 ± 1.5 | 130 ± 35 | 60 ± 5.0 |

[1]Normospermic donors.
[2]Oligoastenoteratospermic donors.
[3]Azoospermic donors.

The values indicate the average and standard deviation obtained from 10 seminal liquid samples from normal donors, 10 seminal liquid samples from oligoastenoteratospermic donors (seminal liquid containing a spermatozoon number lower than 20 millions/ml of semen) and 10 seminal liquid samples from not obstructive azoospermic donors (donors with a spermatozoon number lower than 1 million/ml of semen).

D-aspartic acid value was obtained using a specific HPLC chromatographic method in combination with D-aspartate oxidase. The difference of D-aspartic acid among normospermic and oligoastenoteratospermic donors was significant for P<0.01 and the difference among oligoastenoteratospermic and azoospermic donors also was significant for P<0.01.

These together with other results relating to the activity of D-aspartic acid on LH hormone (luteinizing hormone) and testosterone (Ref. 17 and 18) increments obtained for the rat indicated that the administration of D-aspartic acid to man (daily one or two 3 g doses) for at least 30 days induced an increase of LH and testosterone values and spermatozoon number and motility also in the man (Italian Patent Application RM2005A000468 on September 2005).

The authors of the present invention have now found that the combination of D-aspartic and L-aspartic acids results in a remarkable effectiveness increase compared to the administration of equal amount of alone D-aspartic acid. The authors have carried out studies both on animal and man demonstrating a greater increment of spermatozoon number and motility for the subjects treated with the inventive combination compared to those treated with alone D-aspartic acid. In particular in the man an increase of LH and testosterone hormone levels is observed also.

The results of the study carried out on rabbit and man (not published) indicate that the combination of D-aspartic acid and L-aspartic acids or salts thereof, wherein acids are neutralized as for example with $Na^+$ ion, can be used in order to stimulate the man procreative activity via an increment of spermatozoon number and vitality.

The use of the combination according to the invention for infertility therapy offers the remarkable advantage to be able to carry out only a single daily administration and a cost, for 60-90 day cycle treatment, lower than known therapies.

Therefore it is specific object of present invention a composition comprising or consisting of the combination of D-aspartic and L-aspartic acids or one or more corresponding salts thereof of alkaline or alkaline earth metals, or comprising or consisting of alone L-aspartic acid, said active principles being possibly in combination with one or more pharmaceutically acceptable excipient and/or coadjuvant, for use in the treatment of male infertility.

In the case of combination of D-aspartic and L-aspartic acids or one or more corresponding salts thereof of alkaline or alkaline earth metals, the concentration of D-aspartic acid or salts thereof can vary from 50% to 99.5% while, the concentration of L-aspartic acid or salts thereof can vary from 0.05% to 50%, said percentages being based on total weight of D-aspartic and L-aspartic acids or salts thereof. According to an alternative embodiment, the concentration of D-aspartic acid or salts thereof can vary from 50% to 80% and the concentration of L-aspartic acid or salts thereof can vary from 20% to 50%, said percentages being based on total weight of D-aspartic and L-aspartic acids or salts thereof. According to a preferred embodiment the concentration of D-aspartic acid or salts thereof is 80% and the concentration of L-aspartic acid or salts thereof is 20%, said percentages being based on total weight of D-aspartic and L-aspartic acids or salts thereof. Alternatively, the concentration of D-aspartic acid or salts thereof or of L-aspartic acid or salts thereof is 50%, said percentages being based on total weight of D-aspartic and L-aspartic or salts thereof. According to a further embodiment, the concentration of D-aspartic acid or salts thereof is 99.5% and the concentration of L-aspartic acid or salts thereof is 0.05%, said percentages being based on total weight of D-aspartic and L-aspartic acids or salts thereof.

Preferably, the present invention refers to not obstructive male infertility characterized by oligo and/or astenozoospermia with or without hypogonadotropic hypogonadism.

In particular, the salt of D-aspartic acid or L-aspartic is a sodium salt or a mixture of sodium and potassium or magnesium or zinc salts.

Like above reported, the composition according to the invention can comprise one or more coadjuvants selected from the group consisting of amino acids, vitamins, minerals, reproductive function stimulating hormones, kallikrein, antibiotics, anti-inflammatory agents, antiandrogens, androgens, pentoxifilline, gonadotropine, gonadotropine releasing hormone (GnRH), adrenergic stimulators, dietetic supplements, anti-oxidants (alpha-lipoic acid, Q 10 coenzyme, glutathione and other not here mentioned anti-oxidants), ketoacids as for example oxaloacetic and alpha-ketoglutaric acids. Particularly, amino acids can be chosen from the group consisting of alanine, arginine, carnitine, cysteine, glutamine, glicine, leucine, lisine, isoleucine, methionine, ornithine, phenyl alanine, threonine, tryptophan, valine, serine.

The vitamins can be chosen from the group consisting of vitamin A, C, D3, E, K, B1, B2, B6, B12, PP, biotin (H), folic acid, lipoic acid.

At last, the minerals are chosen from the group consisting of magnesium, potassium, zinc, manganese, molybdenum, chromium, selenium, calcium pantothenate, iron, copper, iodine, phosphorus, fluorine, calcium.

The vitamins can be used at variable concentration as below: vitamin A from 0.0048% to 0.024%, vitamin C from 0.36% to 3.6%, vitamin D3 from 0.00003% to 0.00015%, vitamin E from 0.06% to 0.6%, vitamin K from 0.00042% to 0.0021%, vitamin B1 from 0.0084 to 0.042%, vitamin B2 from 0.0096% to 0.048%, vitamin B6 from 0.012% to 0.06%, vitamin B12 from $6\times10^{-6}\%$ to $3\times10^{-5}\%$, vitamin PP from 0.108% to 0.54%, biotin from 0.0009% to $4.4\times10^{-5}\%$, folic acid from 0.0012% to 0.006%, said percentages being % weight based on total composition weight.

The concentrations of minerals can vary according to the following percentages: magnesium from 3.2% to 9%, potassium from 0.4% to 4%, zinc from 0.09% to 0.450, manganese from 0.02% to 0.070, molybdenum, chromium or selenium from 0.0003% to 0.002%, calcium pantothenate from 0.04% to 0.15%, iron from 0.084% to 0.021%, copper from 0.02% to 0.1%, iodine from 0.0009% to 0.0045%, phosphorus from 2.5% to 20%, fluorine from 0.005% to 0.02%, calcium from 3.24% to 16.2%, said percentages being % weight based on total composition weight.

The concentrations of amino acids in addition to D-aspartic and L-aspartic acids can vary from 0.6% to 10% by weight based on total composition weight.

According to a preferred embodiment of the present invention the composition can comprise, in addition to D- and L-aspartate, folic acid, vitamin B6, vitamin B12 and potassium sorbate and sodium benzoate preservatives. In particular, concentrations can vary as below: folic acid from 0.002% to 0.006%, vitamin B6 from 0.02% to 0.06%, vitamin B12 from $1\times10^{-5}\%$ to $3\times10^{-5}\%$, potassium sorbate from 0.002 to 0.008%, sodium benzoate from 0.002 to 0.008%.

The composition according to the present invention can be administered as daily dose variable from 0.001 g/day to 10 g/day.

Based on above, the concentrations of vitamins and minerals therefore can vary from 30% to 150% of RDA (suggested daily dose). In particular, in Table 3 are reported various compounds and minimum and maximum doses thereof that can be contained in a drug unit dose of the composition according to the invention.

TABLE 3

Minimum and maximum doses of compounds that can be contained in drug unit dose

| Component | Minimum dose. | Maximum dose. |
|---|---|---|
| Vit. A | 240 μcg | 1200 μcg |
| Vit. C | 18 mg | 180 mg (300% RDA) |

TABLE 3-continued

Minimum and maximum doses of compounds that can be contained in drug unit dose

| Component | Minimum dose. | Maximum dose. |
|---|---|---|
| Vit. D3 | 1.5 μcg | 7.5 μcg |
| Vit. E | 3 mg | 30 mg (300% RDA) |
| Vit. K | 21 μcg | 105 μcg |
| Vit. B1 | 0.42 mg | 2.1 mg |
| Vit. B2 | 0.48 mg | 2.4 mg |
| Vit. B6 | 0.6 mg | 3 mg |
| Vit. B12 | 0.3 μcg | 1.5 μcg |
| Vit. PP | 5.4 mg | 27 mg |
| Biotin (h) | 45 μcg | 225 μcg |
| Folic acid | 60 μcg | 300 μcg |
| Magnesium | 90 mg | 450 mg |
| Potassium | 20 mg | 200 mg |
| Zinc | 4.5 mg | 22.5 mg |
| Manganese | 1 mg | 3.5 mg |
| Molybdenum | 15 μcg | 100 μcg |
| Chromium | 15 μcg | 100 μcg |
| Selenium | 15 μcg | 100 μcg |
| Calcium Pantothenate | 2 mg | 7.5 mg |
| Iron | 4.2 mg | 21 mg |
| Copper | 1 mg | 5 mg |
| Iodine | 45 μcg | 225 μcg |
| Phosphorus | 125 mg | 1000 mg |
| Fluorine | 0.25 mg | 1 mg |
| Calcium | 162 mg | 810 mg |
| Alanine | 30 mg | 300 mg |
| Arginine | 30 mg | 300 mg |
| Carnitine | 30 mg | 300 mg |
| Cysteine | 30 mg | 300 mg |
| Glutamine | 30 mg | 300 mg |
| Glycine | 30 mg | 300 mg |
| Leucine | 30 mg | 300 mg |
| Lysine | 30 mg | 300 mg |
| Isoleucine | 30 mg | 300 mg |
| Methionine | 30 mg | 300 mg |
| Ornithine | 30 mg | 300 mg |
| Phenyl alanine | 30 mg | 300 mg |
| Threonine | 30 mg | 300 mg |
| Tryptophan | 30 mg | 300 mg |
| Valine | 30 mg | 300 mg |

Table 4 shows the dosages corresponding to the composition according to the invention with lowest and highest dose/day.

TABLE 4

| Composition | Average dose | Lowest dose | Highest dose |
|---|---|---|---|
| Active principle | | | |
| 1° Composition (80% D-Aspartate e 20% L-Aspartate) | | | |
| Sodium D-Aspartate | 2.49 (g/dose) | 1.24 (g/dose) | 7.47 (g/dose) |
| Sodium L-Aspartate | 0.63 (g/dose) | 0.315 (g/dose) | 1.89 (g/dose) |
| Or | | | |
| 2° Composition (50% D-aspartate e 50% L-Aspartate) | | | |
| Sodium D-Aspartate | 1.56 (g/dose) | 0.78 (g/dose) | 6.24 (g/dose) |
| Sodium L-Aspartate | 1.56 (g/dose) | 0.78 (g/dose) | 6.24 (g/dose) |
| Vitamins | | | |
| Folic acid | 100 μcg/dose | 50 μcg/dose | 300 μcg/dose |
| Vitamin B6 | 1.0 mg/dose | 0.5 mg//dose | 3.0 mg/dose |
| Vitamin B12 | 0.5 μcg//dose | 0.25 μcg//dose | 1.5 μcg/dose |

TABLE 4-continued

| Composition | Average dose | Lowest dose | Highest dose |
|---|---|---|---|
| Preservatives | | | |
| Potassium sorbate | 9 mg/dose | 4.5 mg/dose | 27 mg/dose |
| Sodium benzoate | 9 mg/dose | 4.5 mg/dose | 27 mg/dose |

Moreover, the composition can comprise the following other substances displaying purely a coadjuvant role based on the composition weight of a 3 g commercial dose of active principle.

Xilitol 700, 0.1-10%
Orange Aroma 0.1-10%
Vanilline 0.05-0.5%
Fructose 0.2-20%
Saccharose 0.2-20%
Maltodextrins 0.2-10%;
Aspartame 0.03-0.3%
Pure dehydrated orange juice 0.1-20%%
Magnesium hydroxide 0.1-1%.
Silica 0.1-20%

The percentages are % weight based on the composition weight of a 3.12 g commercial dose of active principle. The composition is in form of salt solution containing 9-11 ml/bottle, or in granule form with 3 g dose of active principle of D/L-aspartate and other ingredients amounting to a 3.5-6.0 g total dry weight.

The present invention now will be described by illustrative but not limitative way, according to preferred embodiments thereof, with detailed reference to enclosed drawings wherein:

FIG. 1 shows LH (luteinizing hormone) increment in human plasma after treatment with the composition according to the invention. Reported values represent the average values and standard deviation (S.D.) obtained from ten 25-40 year old people at time zero and 10, 20 and 30 day after treatment (see bibliography below).

Figure 2:
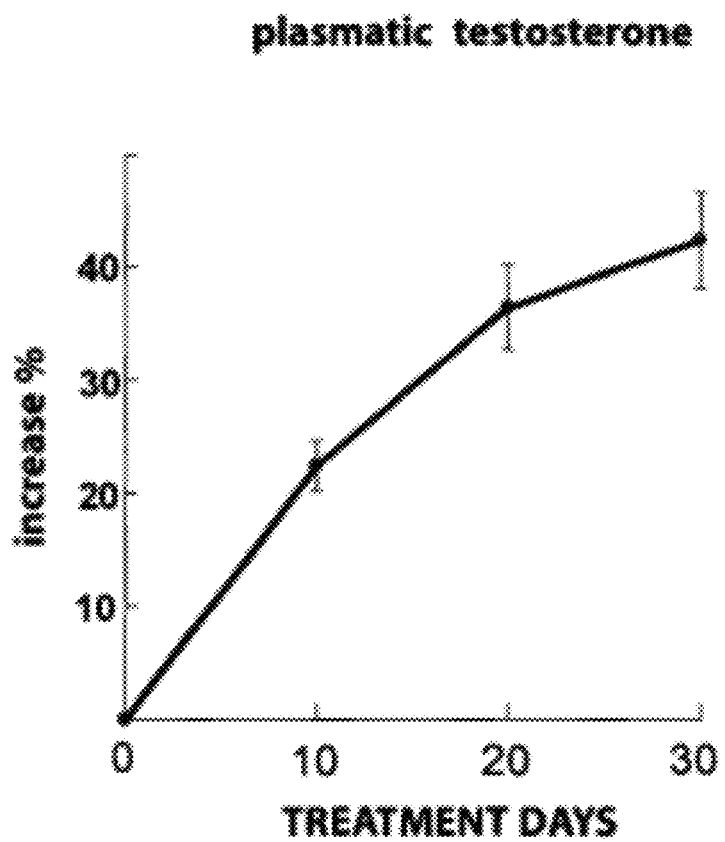

FIG. 2 shows testosterone increment in human plasma after the treatment with the composition according to the invention. Reported values represent the average values and standard deviation (S.D.) obtained from ten 25-40 year old people at time zero and 10, 20 and 30 day after treatment (see bibliography below).

Figure 3:
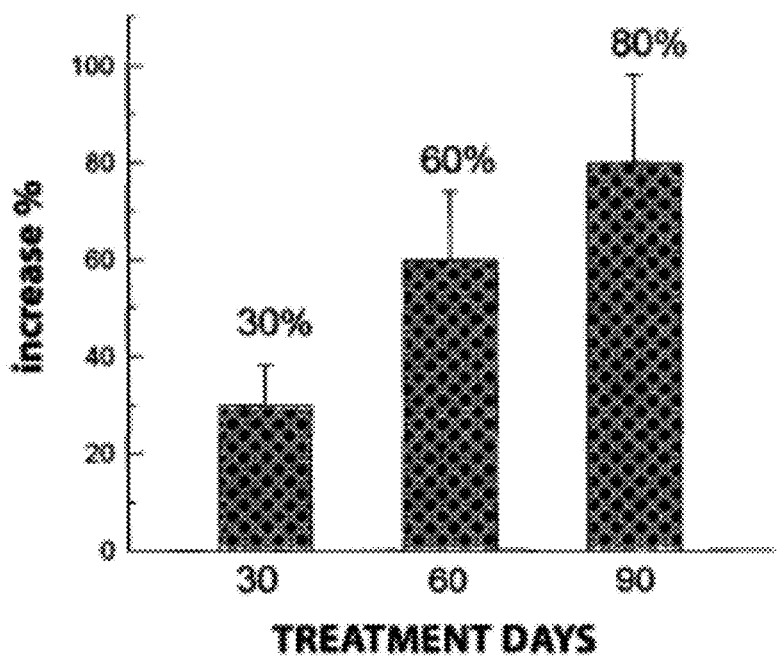

FIG. 3 shows the increment of spermatozoon number in human seminal liquid after treatment with the composition according to the invention (see bibliography below).

Figure 4:
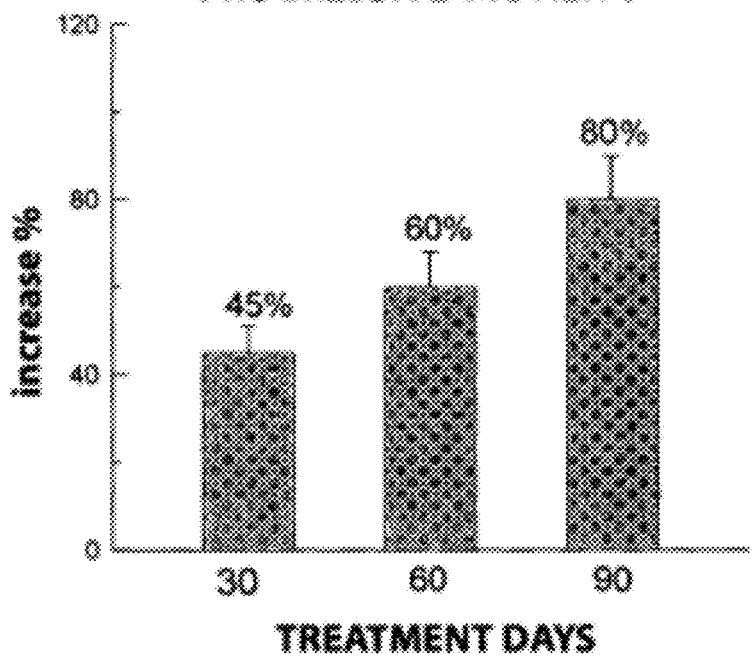

FIG. 4 shows the increment of spermatozoon number in human seminal liquid after treatment with the composition according to the invention. Reported values represent the average values and standard deviation (S.D.) obtained from ten 25-40 year old people at time zero and 30, 60 and 90 day after treatment (see bibliography below).

Figure 5:
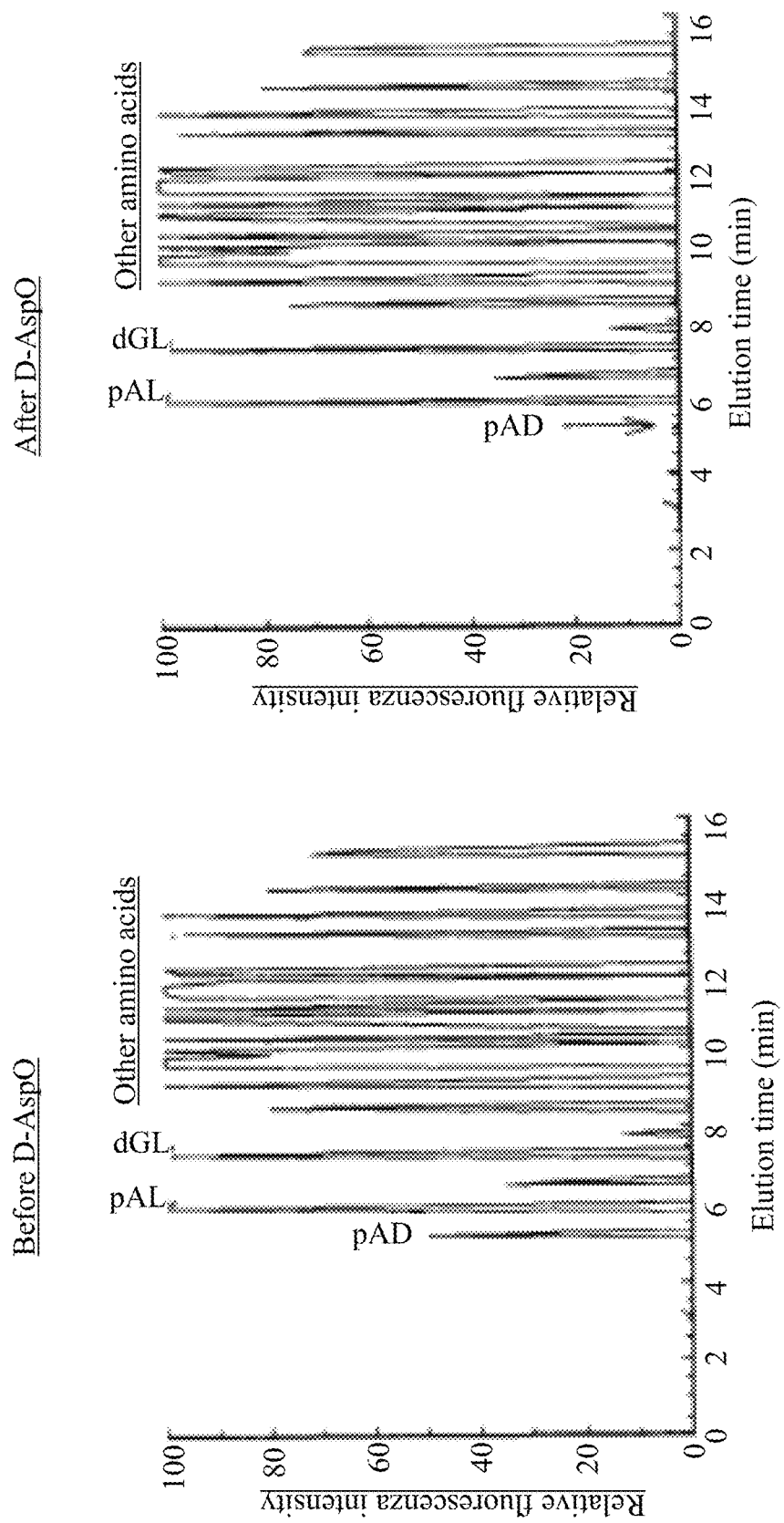

FIG. 5 shows HPLC analysis of known sample consisting of a standard mixture of D-aspartic together with L-amino acid mixture (see bibliography below).

EXAMPLE 1

Preparation of Sodium D-Aspartate and Sodium L-Aspartate Combination in Solution or Powder Form D-aspartic and L-aspartic acids are commercially available in water insoluble powder form. It is necessary therefore the amino acid to be solubilised by sodium, potassium or magnesium salt formation. Herein below an example of preparation of sodium D-aspartate at 2 M concentration, corresponding to 266 g of D-aspartic acid/l in turn corresponding to 312 g of sodium D-aspartate/l, is reported.

Preparation Example of One Litre of Aqueous Mixture Consisting of 80% Sodium D-Aspartate and 20% Sodium L-Aspartate and Packaging in 10 ml/Bottle Mix 212.8 g of D-aspartic acid and 53.2 g of L-aspartic acid in 250 ml of distilled water. Then, under continuous stirring, add portion wise 480 ml of NaOH 4 M (NaOH 4 M corresponds to 160 g/l) and stirring is carried out in order to solubilise D-aspartic acid and L-aspartic acid. After solubilisation the pH of the solution will be 6.0-7.0. If the pH value is higher than 7.0, then adjust to pH 6.0-7.0 with few ml of HCl 2M, if on the contrary the pH is lower than 6.0-7.0, then add more NaOH until the pH value is again 6.0-7.0. Then add 0.9 g of potassium sorbate and 0.9 g of sodium benzoate. Finally add distilled water to a final volume of 1 litre. Filter through 0.45 µm pore membranes (millipore) or 3 MM paper in order to separate insoluble residue and at the same time to sterilize the solution. Successively distribute in 10 ml bottles. Finally add in bottle dosing cap 2 mg of vitamin B6, 0.3 mg of folic acid, 1.5 µcg of vitamin B12 and possibly orange aroma or fructose or other excipient in amount to be established depending on drug desired taste. 10 ml of the solution contain 2.49 g of sodium D-aspartate and 0.63 g of sodium L-aspartate (corresponding to 2.128 g of D-aspartic acid and 0.530 g of L-aspartic acid respectively).

Alternative Procedure

Alternatively above said preparation can be obtained according to the following procedure which is also more practical: Add to 750 ml of 2.66 M NaOH (2.66 M NaOH solution corresponds to 106.6 g of NaOH/l) under stirring 212.8 g of D-aspartic acid and 53.2 g of L-aspartic acid. Continue the stirring until all amino acid is dissolved. After complete solubilisation, check the pH value which must be between 6.0 and 7.0. If pH is higher than 7.0, then add a few ml of 2M HCl until pH is between 6.0 and 7.0. If on the contrary pH is lower than 6.0, then add some ml of 2M NaOH till pH is between 6.0 and 7.0. Then add 0.9 g of potassium sorbate and 0.9 g of sodium benzoate. Finally add distilled water to a final volume of 1 litre. Filter through 0.45 µm pore membranes (millipore) or 3 MM paper in order to separate possible insoluble residue and sterilize the solution. Successively distribute in 10 ml bottles. Finally add in bottle dosing cap 2 mg of vitamin B6, 0.3 mg of folic acid, 1.5 µcg of vitamin B12 and possibly orange aroma or fructose or other excipient in amount to be established depending on drug desired taste. 10 ml of the solution contain 2.49 g of sodium D-aspartate and 0.63 g of sodium L-aspartate (corresponding to 2.128 g of D-aspartic acid and 0.530 g of L-aspartic acid respectively).

Preparation Example of 1 l Aqueous Solution of Sodium D-Aspartate Alone

Mix 266 g of D-aspartic acid in 250 ml of distilled water. Then under stirring, add 480 ml of NaOH 4 M (a solution of NaOH 4 M corresponds to 160 g/l) and stir in order to solubilise D-aspartic acid. After solubilisation the pH of the solution must be between 6.0-7.0. If the pH is higher than 7.0, then adjust pH to 6.0-7.0 with a few ml of 2 M HCl.

If on the contrary the pH is lower than 6.0-7.0, then add more NaOH until the pH is 6.0-7.0. Then add 0.9 g of potassium sorbate and 0.9 g of sodium benzoate. Finally add distilled water to a final volume of 1 litre. Filter through 0.45 µm pore membranes (millipore) or 3 MM paper in order to separate insoluble residue and at the same time to sterilize the solution. Successively distribute in 10 ml bottles. Finally add in bottle dosing cap 2 mg of vitamin B6, 0.3 mg of folic acid, 1.5 µcg of vitamin B12 and possibly orange aroma or fructose or other excipient in amount to be established depending on drug desired taste. 10 ml of the solution contain 3.12 g of sodium D-aspartate corresponding to 2.66 g of D-aspartic acid.

As an alternative to above procedure the sodium D-aspartate solution is prepared as below: Add to 750 ml of NaOH 2.66 M (NaOH 2.66 M corresponds to 106.6 g of NaOH/litre) add under agitation 266 g D-aspartic acid. Stir continuously until all the D-aspartic is dissolved. After solubilisation the pH of the solution must be between 6.0-7.0. If it is higher than 7.0, then adjust pH to 6.0-7.0 with few ml of 2 M HCl. If on the contrary the pH is lower than 6.0-7.0, then add more NaOH until the pH is 6.0-7.0. Then add 0.9 g of potassium sorbate and 0.9 g of sodium benzoate. Finally add distilled water to a final volume of 1 litre. Filter through 0.45 µm pore membranes (millipore) or 3 MM paper in order to separate insoluble residue and at the same time to sterilize the solution. Successively distribute in 10 ml bottles. Finally add in bottle dosing cap 2 mg of vitamin B6, 0.3 mg of folic acid, 1.5 µcg of vitamin B12 and possibly orange aroma or fructose or other excipient in amount to be established depending on drug desired taste. 10 ml of the solution contain 3.12 g of sodium D-aspartate corresponding to 2.66 g of D-aspartic acid.

Preparation Example of One Litre of Aqueous Mixture Consisting of 50% Sodium D-Aspartate and 50% Sodium L-Aspartate and Packaging in 10 ml Bottles Mix 133 g of D-aspartic acid and 133 g of L-aspartic acid in 250 ml of distilled water. Then, under continuous stirring, add 480 ml of NaOH 4 M (4 M=160 g/l) and stir in order to solubilise D-aspartic acid and L-aspartic acid. After solubilisation the pH of the solution will be 6.0-7.0. If the pH value is higher than 7.0, then adjust to pH 6.0-7.0 with few ml of HCl 2M. If on the contrary the pH is lower than 6.0-7.0, then add more NaOH until the pH value is again 6.0-7.0. Then add 0.9 g of potassium sorbate and 0.9 g of sodium benzoate. Finally add distilled water to a final volume of 1 litre. Filter through 0.45 µm pore membranes (millipore) or 3 MM paper in order to separate insoluble residue and at the same time to sterilize the solution. Successively distribute in 10 ml bottles. Finally add in bottle dosing cap 2 mg of vitamin B6, 0.3 mg of folic acid, 1.5 µcg of vitamin B12 and possibly orange aroma or fructose or other excipient in amount to be established depending on drug desired taste. 10 ml of the solution contain 1.56 g of sodium D-aspartate and 1.56 g of sodium L-aspartate (corresponding to 1.33 g of D-aspartic acid and 1.33 g of L-aspartic acid respectively).

As an alternative to above procedure the preparation of the mix of sodium D-aspartate and sodium L-aspartate is carried out as below: Add to 750 ml of 2.66 M NaOH (2.66 M NaOH=106.6 g of NaOH/l) under constant stirring 133 g of D-aspartic acid and 133 g of L-aspartic acid. Continue the stirring until all amino acid is dissolved. After complete solubilisation, check the pH value which must be between 6.0 and 7.0. If pH is higher than 7.0, then add few ml of 2M HCl until pH is between 6.0 and 7.0. If on the contrary pH is lower than 6.0-7.0, then add more 2M NaOH till pH is between 6.0 and 7.0. Then add 0.9 g of potassium sorbate and 0.9 g of sodium benzoate. Finally add distilled water to a final volume of 1 litre. Filter through 0.45 μm pore membranes (millipore) or 3 MM paper in order to separate possible insoluble residue and sterilize the solution. Successively distribute in 10 ml bottles. Finally add in bottle dosing cap 2 mg of vitamin B6, 0.3 mg of folic acid, 1.5 μcg of vitamin B12 and possibly orange aroma or fructose or other excipient in amount to be established depending on drug desired taste. 10 ml of the solution contain 1.56 g of sodium D-aspartate and 1.56 g of sodium L-aspartate (corresponding to 1.33 g of D-aspartic acid and 1.33 g of L-aspartic acid).

Preparation of Sodium D-Aspartate and Sodium L-Aspartate in Powder Form

D-aspartate and L-aspartate as sodium or potassium or magnesium salts are commercially available. DL-aspartate sodium salt, consisting of DL-aspartate racemic mixture, i.e. 50% sodium D-aspartate and 50% sodium L-aspartate, is also commercially available. Therefore, it is also possible monodose sachets containing determined dose of sodium D-aspartate (3.12 g), to be prepared. To this dose 2 mg of B6 vitamin, 0.3 mg of folic acid and 1.5 μcg of B12 vitamin and possibly determined amounts of orange or other aroma, saccharose or other excipients in order to have a palatable ingestion, are then added. In this preparation nor sodium benzoate neither potassium sorbate are added being drug in powder form and thus not microorganism contaminable. Then the sachet is dissolved in drinkable water and ingested.

EXAMPLE 2

Study about the Effects of a Combination of 80% Sodium D-Aspartate and 20% Sodium L-Aspartate on Rabbits The study has been carried out on two groups of rabbits (10 rabbits for each group) in order to test the effect of sodium D-aspartate and of the sodium D-aspartate in combination with a determined amount of sodium L-aspartate on the quality of seminal liquid, i.e. on number of spermatozoa/ml and on the progressive quick motility thereof.

The experiment involved the ingestion by a group of 10 male adult rabbits, 6 month old, of an amount of sodium D-aspartate corresponding to 0.250 g daily (1.6 μmoli/rabbit; 0.26 μmoli/kg of body weight) over 20 days. Practically, sodium D-aspartate was mixed with food in such amount that the food daily ingested by the rabbit contained 0.250 g of sodium D-aspartate. In the same way, in a second experiment carried out on another group of 10 same age male adult rabbits, a mixture consisting of 0.2 g of sodium D-aspartate and 0.05 g of sodium L-aspartate (80% D-Asp: 20% L-Asp) was administered. Before the start of the experiment and at the end of drug ingestion lasting 20 days, from every rabbit a sperm sample obtained by stimulation using an artificial vagina has been collected and the total number of spermatozoa/ml of ejaculate and motility thereof have been determined.

The number of the spermatozoa and progressive quick motility are determined according to (World Health Organization) WHO guidelines using a Makler Chamber for the count (Sefi Medtstl Instrument, Haifa, Israel) and in the same place the progressive quick motility has been determined. The rabbit semen was 1:10 diluted in an iso-osmotic solution due to excessive concentration.

The result obtained from this study demonstrated that in the first experiment, i.e. rabbits treated with alone sodium D-aspartate, this amino acid statistically improved the spermatozoon number in seminal liquid, i.e. the production, on average, by 19.3%. From an average value of 300.000.000 spermatozoa/ml of seminal liquid for control rabbits (collection before the treatment start) to an average value of 358.000.000/ml after the ingestion of sodium D-aspartate for 20 days, corresponding to a 19.3% increase (Table 5; part A; 1° group of 10 rabbits). Moreover, in the same seminal liquids of treated rabbits, also an improvement of spermatozoon progressive quick motility varying from 40% to 55%, that is 37% increase compared to the control values, has been detected (Table 5, part B, 1° group of rabbits).

In the second experiment carried out with other same age 10 rabbits administered with a daily dose consisting of 0.2 g of sodium D-aspartate and 0.05 g of sodium L-aspartate (D-Asp 80%: L-Asp 20%) and for the same time, the quality of seminal liquid was further improved. In this case, in fact, the number of spermatozoa in the seminal liquid before the treatment was 320.000.000 spermatozoa/ml as average value, while after the treatment with sodium L-aspartate integrated sodium D-aspartate, was 410.000.000/ml spermatozoa/ml of seminal value, that is increase by 28.1% (Table 5; part A; 2° group of rabbits). Moreover, also the progressive quick motility of the spermatozoa was statistically improved. In fact, progressive quick spermatozoa found in seminal liquid of rabbit first group amount to 40% while after the treatment with D-aspartate the average value thereof was 55%, that is increase by 37%. For results after the ingestion of the mixture consisting of sodium D-aspartate and sodium L-aspartate see Table 5, part B; 2° group of rabbits. In second group of rabbits administered with D-Asp+L-aspartate the average value of quick spermatozoa number varied from 39% to 58%, that is increase by 48% (Table 5; part B; 2° group of rabbits).

From a statistical point of view, the improvements of studied parameters, both using sodium D-aspartate alone and using a mixture consisting of sodium L-aspartate integrated sodium D-aspartate, analyzed using Student T test were all significant for $P<0.01$. Above reported results are shown in below reported Table 5 showing the effect of sodium D-aspartate and D-aspartate+sodium L-aspartate on the improvement of number and quality of the spermatozoa in rabbit seminal liquid.

TABLE 5

Effect of sodium D-aspartate and sodium DL-aspartate on the improvement of number and quality of the spermatozoa in rabbit seminal liquid Number of spermatozoa/ml of seminal liquid in rabbits:

|  | 1° group of 10 rabbits | | 2° group of 10 rabbits | |
| --- | --- | --- | --- | --- |
|  | Before the treatment | After ingestion of 100% D-Aspartate | Before the treatment | After ingestion of 80% D-Aspartate + 20% L-Aspartate |
| Part A | | | | |
|  | 300.000.000/ml seminal liquid | 358.000.000/ml seminal liquid | 320.000.000/ml seminal liquid | 410.000.000/ml seminal liquid |
| % increment | — | 19.3% | — | 28.1% |
| Part B | | | | |
| Quick progressive | 40%* | 55%* | 39%* | 58%* |
| % increment) | — | 37% | — | +48% |
| Slow | 30%* | 27%* | 28%* | 28%* |
| Immobile | 30%* | 18%* | 33%* | 14%* |

The results are referred to average values obtained on one group of 10 adult rabbits (6 month old) before the treatment and 20 days after the ingestion of 0.25 g sodium D-aspartate (1.60 μmole/rabbit; 0.26 μmol/kg of body weight) and on a group of other same age 10 rabbits before the treatment and 20 days after the ingestion of a mixture consisting of 0.2 g of sodium D-aspartate and 0.05 g of sodium L-aspartate daily and for 30 days (80% of Na-D-aspartate and 20% of Na-L-aspartate).

Values reported in part A of the table are referred to total number of spermatozoa/ml of seminal liquid before and after respective drug treatment. In parenthesis the percentage of increment of spermatozoa number is reported.

In part B of the table the values with asterisk are referred to percentage values of number of quick progressive, slow, immobile spermatozoa on 100 base. The values in parenthesis are referred to the percentage of the increases of quick progressive spermatozoa with respect to values before respective drug treatment.

The increases of spermatozoa number and motility in rabbits treated with sodium D-aspartate and sodium L-aspartate integrated sodium D-aspartate are all significant (Student T; P<0.01).

EXAMPLE 3

Study about the Effects of a Combination of Sodium D-Aspartate 50% and Sodium L-Aspartate 50% in the Rabbits The study involved the administration of a mixture consisting of 0.125 g of sodium D-aspartate+0,125 g of sodium L-aspartate (D-Asp 50%: L-Asp 50%) to a group of 10 rabbits according to procedure of Example 2. The obtained result shows that also in this case an improvement of semen quality was obtained in terms of total number of spermatozoa and progressive quick motility compared to controls but this effect was little less efficient with respect to the effect from the use of the mixture consisting of 80% sodium D-aspartate and 20% sodium L-aspartate. In this case the production of the number of spermatozoa was increased by 25% and motility by 55% compared to controls showing that also in this case an improvement compared to D-aspartate alone was obtained but it was lower than mixture consisting of 80% D-aspartate and 20% L-aspartate.

EXAMPLE 4

Study about the Effects of a Combination of 80% Sodium D-Aspartate and 20% Sodium L-Aspartate on Man 25-40 year old volunteer groups have been recruited and the effect of alone sodium D-aspartate and the effect of sodium L-aspartate supplemented sodium L-aspartate on human spermatogenesis have been evaluated.

The study involves the oral ingestion (after breakfast or main meal) by a group of 10 25-40 year old people of a daily dose consisting of 3.12 g of sodium D-aspartate (19.2 μmole of sodium D-aspartate; 0.27 μmol/kg of body weight for a 70 kg person) over 30 days. Another group of 10 25-40 year old people (after breakfast or main meal) ingested a daily dose of a mixture consisting of 2.49 g of sodium D-aspartate and 0.63 g of sodium L-aspartate (80% sodium D-aspartate and 20% sodium L-aspartate) for the same period.

Before the start of the study and on serum derived from blood collected after 10, 20 and 30 days of treatment the values of LH, testosterone and number and progressive quick motility of the spermatozoa have been determined.

LH and testosterone hormonal assays have been carried out using specific commercial kits for clinical chemical use.

Seminal liquid has been collected through masturbation after 3-5 abstinence days. The number of the spermatozoa and progressive quick motility thereof have been determined according to (World Health Organization) WHO guidelines using a Makler Chamber for the count (Sefi Medtstl Instrument, Haifa, Israel) and in the same place the progressive quick motility has been determined.

It is to be pointed out that this study has been carried out on selected subjects having a number of spermatozoa in seminal liquid from 15.000.000 to 20.000.000/ml, that is minimum threshold values within normal range. This expedient has been based on preliminary studies indicating that the effect of D-aspartate on the improvement of the spermatogenesis was appreciated with greater evidence in subjects producing a not too much high spermatozoon number. Likely this results from the fact that subjects producing a relatively low number of spermatozoa, have also an higher % of spermatozoa not reaching the maturation and degraded during the spermatogenesis. In this case therefore the action of D-aspartate stimulates their maturation to vital spermatozoa.

Obtained result indicated that the use of sodium D-aspartate statistically improved the values of LH and testosterone hormones (specific hormones involved in spermatogenesis) and number and progressive quick motility of spermatozoa. Specifically the daily treatment with 3.12 g of sodium D-aspartate induced an average increase of LH haematic values by 25.6%. From an average value of 4.3 mUI/ml for the controls, was obtained a value of 5.4 mUI/ml in people after the ingestion of D-aspartate (P<0.01). The same effect was observed for testosterone passing from a serum value of 4.8 ng/ml before the treatment to a serum value of 6.3 ng/ml after the treatment, that is a 31.2% increase (P<0.01) (Table 6, part A, 1° group of people). Moreover, also the number and spermatozoon progressive motility are meaningfully increased compared to controls. In this case in fact the total number of spermatozoa found before the ingestion of D-aspartate was 18.000.000 and after the treatment with D-Aspartate 23.000.000, both as average, therefore a 27% increase (Table 6, part B; first group of 10 people). Moreover, also the motility has been significantly increased by 28% after treatment with D-aspartate compared to values before the treatment (Table 6, part B, 1° group of 10 people) (P<0.01).

Interestingly, it has been further observed that as for rabbits (see above), also for man the treatment with a mixture consisting of sodium L-aspartate integrated sodium D-aspartate resulted in an ulterior improvement compared to the use of alone sodium D-aspartate both for haematic hormones (LH and testosterone) and quality of seminal liquid. In this second experiment, in fact, we observed that the group of people who had assumed the daily dose consisting of 2.49 g of sodium D-aspartate and 0.63 g of sodium L-aspartate (80% D-Asp; 20% L-Asp) further improves the fertility performance compared to control. LH average value increased by 38.6% compared to control (same people before the treatment) versus a 25.6% increment observed using alone sodium D-aspartate (Table 6, part A; 2° group of 10 people). The same phenomenon occurs for testosterone. This steroidal hormone, in fact, after treatment with L-aspartate integrated D-aspartate is increased by 47.8% compared to control (same people before the start of therapy), while using alone D-aspartate the increment was by 31.2% (Table 6, part A; second group of 10 people). Moreover, also the number and motility of the spermatozoa were improved. From an average value of 19.500.000/ml before the therapy to a value of 28.000.000/ml, an improvement by 43% (Table 6, part B; 2° group of 10 people). Moreover, with the last treatment, an improvement of spermatozoon quality was also obtained. In fact, the number of quick progressive spermatozoa obtained with the use of sodium L-aspartate co-adjuvated sodium D-aspartate passed from 34% to 50% values before and after the treatment respectively, that is a 47% increase (Table 6, part B; 2° group of 10 people). Table 6 shows the effect of sodium D-aspartate and sodium D-aspartate+sodium L-aspartate on the improvement of LH and testosterone hormones and on number and quality of spermatozoa in human seminal liquid.

TABLE 6

Effect of sodium D-aspartate and mixture consisting of 80% sodium D-aspartate and 20% sodium L-aspartate on the increase of LH e testosterone hormones in human serum and number and quality of spermatozoa in human seminal liquid

| | 1° group of 10 people | | 2° group of 10 people | |
| --- | --- | --- | --- | --- |
| | Before the treatment | After ingestion of 100% D-Aspartate | Before the treatment | After ingestion of 80% D-Aspartate + 20% L-Aspartate |
| Part A Concentration of LH and testosterone in human serum | | | | |
| LH (mIU/ml serum) | 4.3 | 5.4 | 4.4 | 6.1 |
| % increment | — | +25.6% | — | +38.6% |
| Testosterone (ng/ml serum) | 4.8 | 6.3 | 4.6 | 6.8 |
| % increment | — | +31.2% | — | +47.8% |
| Part B Number and quality of spermatozoa in human seminal liquid | | | | |
| N. total spermatozoa/ml seminal liquid | 18.000.000 | 23.000.000 | 19.500.000 | 28.000.000 |
| | | +27% | | +43% |
| Quick progressive spermatozoa | 35%* | 45%* | 34%* | 55%* |
| | — | +28% | — | +61% |
| Slow spermatozoa | 30%* | 25%* | 28%* | 29%* |
| Immobile spermatozoa | 35%* | 30%* | 38%* | 21%* |

The results are referred to average values from a number of 10 25-40 year old subjects before treatment and after daily ingestion for 30 days of 3.0 g of sodium D-aspartate/day (1° group of 10 people) and a group of 10 same age subjects before treatment and after daily ingestion for 30 days of 2.49 g of sodium D-aspartate and 0.63 g of sodium L-aspartate (80% sodium D-aspartate and 20% sodium L-aspartate). The values in parenthesis in part A of the table are referred to % increment of LH and testosterone before and after respective treatment. The values with asterisk of part B of the table are referred to % value of the number of quick progressive, slow, immobile spermatozoa on base 100.

The values in parenthesis of part B of the table are referred to % increases of total and quick progressive spermatozoa.

The increases of all the values in parenthesis (LH, testosterone, total number and quick progressive spermatozoa) are all significant (T Student; $P<0.01$).

The results obtained from these experiments demonstrated that the values of LH and testosterone increase meaningfully over treatment days and up to approximately 30 days of treatment compared to basal value (before the treatment). Successively such increase remains constant if the treatment continues for an ulterior period of time. On the contrary the number of the spermatozoa in seminal liquid continues to increase progressively up 90° day of therapy.

In FIGS. 1 and 2 the diagram of increased values for LH and testosterone in human blood before and after treatment with the composition according to the invention (80% sodium D-aspartate and 20% sodium L-aspartate) is reported.

In FIGS. 3 and 4 the diagram of increased values of the number of spermatozoa and their progressive quick motility before and after treatment with the composition according to the invention is reported.

Determination of D-Aspartic Acid in Human Seminal Liquid 2 ml of seminal liquid obtained them from each patient is diluted in 10 ml of 0.2 M TCA (trichloro acetic acid) for deproteneization and centrifuged at 10.000 rpm for 30 min. The supernatant containing D-aspartic acid and other amino acids, was purified on a cation exchange column (1×4 cm) as described in Ref. 18-21. Briefly to a 2×4 AG-50W-X8; 200-400 mesh, Bio-Rad, ion-exchange resin column the above obtained TCA supernatant of seminal liquid was added. After sample absorption, the column was washed with 10 ml of 0.001 M HCl and then eluted with 10 ml of 4 M ammonium hydroxide. This eluate, containing purified amino acids, was dried on warm plate to eliminate ammonia and the residue was dissolved in 2 ml of distilled water and D-aspartic acid was determined by HPLC or a colorimetric method based on the use of D-aspartate oxidase (purified from bovine kidney) as reported in our paper (Ref: 18-21).

FIG. 5 shows an example of HPLC analysis of a standard sample consisting of a standard mixture of D-aspartic together with L-amino acid mixture.

Left panel shows HPLC analysis of a standard mixture consisting of D-Asp and other L-amino acids. The diagram represents an example of a chromatogram obtained using 10 picomol of D-Asp and 20 picomol of following other amino acids: Glu, Asn, Gln, Ser, Thr, His, Gly, Arg, Wing, Taurine, GABA, Tyr, Val, Met, Leu, Ile, Phe and Lys. e D-Asp is eluted at 5.2 min followed by L-Asp and other L-amino acids.

Right panel refers to same sample, but after treatment with D-aspartate oxidase. In this case D-aspartate oxidase enzyme which is specific for the oxidation of only D-Asp eliminated the peak at 5.2 min elution time thus confirming that this peak really resulted from D-aspartic acid.

Statistical Analysis

The data is expressed as average±SD using Student T test. $P<0.05$ has been considered statistically significant.

EXAMPLE 5

Study about Effects of a Combination of 50% Sodium D-Aspartate and 50% Sodium L-Aspartate on Man A further study involving the treatment of another group of 10 25-40 year old people with a mixture consisting of 1.56 g of sodium D-aspartate+1.56 g of sodium L-aspartate (50% D-Asp: 50% L-Asp) as daily dose for 30 days has been carried out. Obtained results indicated that also in this case an improvement both of LH and testosterone haematic values and the quality of the seminal liquid was obtained, but less efficient compared to use of the mixture consisting of 80% sodium D-aspartate and 20% sodium L-aspartate. In this case in fact LH and testosterone values increased significantly i.e. by 30% and 38%, respectively, compared to basic values. Moreover, also the number of the spermatozoa and the progressive quick motility thereof were increased significantly by 45% compared to controls (data not shown in table). Therefore also using D-Asp+L-Asp a very significant improvement of spermatic parameters was observed, but lower than using 80% D-Asp and 20% L-Asp.

In conclusion, as observed for the rabbits, also for the man the treatment with sodium L-aspartate integrated sodium D-aspartate results in a significant improvement both of LH and testosterone values in the blood and spermatozoon number and motility in seminal liquid compared to treatment consisting of the use of alone sodium D-aspartate.

EXAMPLE 6

Preparation of Rabbit Feed Containing Several Combinations of D-Aspartic and L-Aspartic Acids

EXAMPLE 6A

Preparation of Feed Containing a Combination of 80% D-Aspartic and 20% of L-Aspartic Acids.

2 kg of rabbit feed in 4 litres of distilled water are mixer homogenized at 60-70° C. up to formation of a homogenous mixture. Then 9.12 g of D-aspartic acid and 2.28 g of L-aspartic acid (totally 11.4 g) are added and the mixture is again homogenized to obtain an homogenous dispersion of D-aspartic and L-aspartic acids in feed knead. Finally water is evaporated by oven heating until the feed is again hard. The feed is cooled, cut in 5-10 g cubes and used for animal feeding.

In this way, 1 g of food will contain 4.56 mg of D-aspartic acid and 1.14 mg of L-aspartic acid.

EXAMPLE 6B

Preparation of Feed Containing a Combination of 50% D-Aspartic and 50% of L-Aspartic Acids 2 kg of rabbit feed in 4 litres of distilled water are mixer homogenized at 60-70° C. up to formation of a homogenous mixture. Then 5.7 g of D-aspartic acid and 5.7 g of L-aspartic acid (totally 11.4 g) are added and the mixture is again homogenized to obtain an homogenous dispersion of D-aspartic and L-aspartic acids in feed knead. Finally water is evaporated by oven or low fire heating until the feed is again hard. The feed is cooled, cut in 5-10 g cubes and used for animal feeding.

In this way, 1 g of food will contain 2.85 mg of D-aspartic acid and 2.85 mg of L-aspartic acid.

EXAMPLE 6C

Preparation of Feed Containing a Combination of 99.5% D-Aspartic and 0.05% L-Aspartic Acids 2 kg of rabbit or rat feed in 4 litres of distilled water are kitchen mixer homogenized at 60-70° C. up to formation of a homogenous mixture. Then 11.43 g of D-aspartic acid and 0.570 g of L-aspartic acid (totally 11.4 g) are added and the mixture is again homogenized to obtain an homogenous dispersion of D-aspartic and L-aspartic acids in feed knead. Finally water is evaporated by oven or low fire heating until the feed is again hard. The feed is cooled, cut in 5-10 g cubes and used for animal feeding.

In this way, 1 g of food will contain 5.67 mg of D-aspartic acid and 0.03 mg of L-aspartic acid.

EXAMPLE 6D

Preparation of Feed Containing Only D-Aspartic Acid or Only L-Aspartic Acid 2 kg of rabbit or rat feed in 4 litres of distilled water are mixer homogenized at 60-70° C. up to formation of a homogenous mixture. Then 11.4 g of D-aspartic acid or 11.4 g of L-aspartic acid are added and the mixture is again homogenized to obtain an homogenous dispersion of D-aspartic acid or L-aspartic acid in feed knead. Finally water is evaporated by oven or low fire heating until the feed is again hard. The feed is cooled, cut in 5-10 g cubes and used for animal feeding.

In this way, 1 g of food will contain 5.7 mg of D-aspartic acid or 5.7 mg of L-aspartic acid.

EXAMPLE 7

Study about the Effects of a Combination of 80% D-Aspartic and 20% L-Aspartic Acid on Spermatozoon Number and Motility of Rabbit The study has been carried out on two groups of rabbits. A first group consisting of 10 rabbits having 6 month old (approximately 5 kg of body weight) fed for 20 days with food mixture containing the mixture of 80% D-aspartic and 20% L-aspartic acids (see above: "Example of preparation of feed containing a combination of 80% D-aspartic acid and 20% L-aspartic acid"). A same age second group of 10 rabbits representing a control group (or placebo) was fed eat for 20 days with same type food as above prepared, but without the addition of D-aspartic and L-aspartic acids mixture. The experiments have been carried out in a rabbit breeding farm ("Potenza Breeders' Association", Potenza, Italy). Before the start and at the end of the experiment from each rabbit a sperm sample has been collected by stimulation with an artificial vagina (see paper: "G. Macchia et al., DL-aspartic acid administration improve semen quality in rabbit bucks, published on "Animal Reproduction Science, 118, 337-343, 2010) and the total number of spermatozoa/ml of ejaculate and motility thereof have been determined.

The number of the spermatozoa and progressive quick motility are determined according to (World Health Organization) WHO guidelines using a Makler Chamber for the count (Sefi Medtstl Instrument, Haifa, Israel) and in the same place the progressive quick motility has been determined. The rabbit semen was 1:10 diluted in an iso-osmotic solution due to excessive concentration and then analysed (note: each rabbit weighed approximately 5 kg and consumed approximately 200 g of food daily. Since 1 g of feed contained 4.56 mg of D-aspartic acid and 1.14 mg of L-aspartic acid it resulted that in a day the rabbit assumed a total of 912 mg of D-aspartic acid and 228 mg of L-aspartic acid).

The result obtained from this study demonstrated that the ingestion of the 80% D-aspartic acid and 20% L-aspartic acid mixture statistically improved the spermatozoon number in seminal liquid, i.e. the production, on average, by 22%. From an average value of 320.000.000 spermatozoa/ml of seminal liquid for rabbits before the treatment to an average value of 358.000.000/ml after the ingestion of D-aspartic and L-aspartic acid mixture (Table 7; part A; 1° group of 10 rabbits). Moreover, in the same seminal liquids of treated rabbits, also an improvement of spermatozoon progressive quick motility varying from 38% (this percentage refers to the number of quick progressive spermatozoa out of a total number of 100 microscope observed spermatozoa) to 54%, both as average value, that is an increase of 1.42 times with P<0.01 significance (Table 7, part B, 1° group of rabbits) was observed.

In the group of rabbits, i.e. control group (or placebo), no statistical significant improvement both of total number of spermatozoa/ml of seminal liquid (Table 7, part A, 2° group of rabbits) and motility thereof (Table 7, part B, 2° group of rabbits).

TABLE 7

Effect of a mixture consisting of 80% D-aspartic acid and 20% L-aspartic acid on the increase number and quality of spermatozoa in rabbit seminal liquid

| | 1° group of rabbits Treatment | | 2° group of rabbits Control | |
| --- | --- | --- | --- | --- |
| | Before treatment | After treatment 80% D-Asp acid 20% L-Asp acid | Before treatment | After placebo treatment |
| Part A: Effect on spermatozoon number in seminal liquid | | | | |
| Increment | 320.000.000/ml seminal liquid | 390.000.000/ml seminal liquid +22% | 310.000.000/ml seminal liquid | 315.000.000/ml seminal liquid +1.6% |
| Part B: Effect on spermatozoon rate | | | | |
| Quick motility | 38% | 56% | 37% | 38% |
| Increment | | +42% | | +2% |
| Slow motility | 25% | 27% | 27% | 28% |
| Immobile | 37% | 17% | 36% | 34% |

The results report average values for a group of 10 adult rabbits (6 month old: approximately 5 kg of body weight) before the treatment and 20 days after the ingestion of D-aspartic and L-aspartic acids mixture. The amount of the amino acid ingested daily by the rabbit was o 912 mg of D-aspartic acid and 228 mg of L-aspartic acid.

Values reported in part A of the table refer to average number of spermatozoa/ml of seminal liquid before the drug treatment and after 20 days of treatment.

Values reported in part B of the table refer to spermatozoon motility in terms of quick, slow and immobile spermatozoa on base 100.

The increases of spermatozoon number and motility thereof in rabbits treated with D-aspartic and L-aspartic acid mixture are all significant ones. (Student T=P<0.01).

EXAMPLE 8

Study of the Effects of a Combination of 50% D-Aspartic Acid and 50% L-Aspartic Acid on the Number and Motility of Rabbit Spermatozoa Also this study has been carried out on two groups of same age and weight rabbits as used for previous study. As a difference in this case to the rabbit treated group was administered a feed containing a mixture of 50% D-aspartic acid and 50% L-aspartic acid for 20 days (see above preparation: "Example of preparation of feed containing a combination of 50% D-aspartic acid and 50% L-aspartic acid"), and a second 10 rabbit group was used as a control. Also in this case seminal liquid has been collected before and after the experiment and then examined for spermatozoon number and motility thereof.

The results obtained from this study demonstrated that also using a mixture consisting of 50% D-aspartic acid and 50% L-aspartic acid an improvement of the production, i.e. number, of spermatozoa in seminal liquid them and motility thereof was obtained (see table 8). In fact, as reported in table 8, with this treatment a 16% increment of spermatozoon number, significant for P<0.01, and also an increment of motility thereof by 1.27 times, again significant for P<0.01, have been obtained. In table 8 obtained results are detailed.

The results report average values obtained for a group of adult rabbits (6 month old: approximately 5 kg of body weight) before and after 20 day treatment by ingestion of the D-aspartic and L-aspartic acids mixture. The amounts of amino acid administered to rabbits daily was 570 mg of D-aspartic acid and 570 mg of L-aspartic acid.

Values reported in part A of the table refer to average number of spermatozoa/ml of seminal liquid before the drug treatment and after 20 days of treatment.

Values reported in part B of the table refer to spermatozoon motility in terms of quick, slow and immobile spermatozoa on base 100.

The increases of spermatozoon number and motility thereof in rabbits treated with D-aspartic and L-aspartic acid mixture are all significant ones. (Student T=P<0.01).

For control rabbits reference is made to the same rabbit group as reported in table 7.

EXAMPLE 9

Study about the Effects of a Combination of 99.5% D-Aspartic Acid and 0.05% L-Aspartic Acid on Number and Motility of the Spermatozoa on Rabbits Also this study carried out on rabbits has been carried out in the same way as previous ones. As a difference in this case to the rabbit treated group was administered a feed containing a mixture of D-aspartic and L-aspartic acid at 99.5:0.05 ratio (see above Example 3: "Preparation of feed containing a combi-nation of 99.5% D-aspartic acid and 0.05% L-aspartic acid"). Also in this case total amount of D-Asp+L-Asp ingested daily by rabbits was about 1.140 g.

The results obtained from this study demonstrated that also using the mixture consisting of 99.5% D-aspartic acid and 0.05% L-aspartic acid a 18.6% improvement of the production, i.e. number, of spermatozoa in seminal liquid and a 31% (+1.31) increment of quick motility thereof were obtained (see table 9).

TABLE 8

Effect of a mixture consisting of 50% D-aspartic acid and 50% L-aspartic acid on the increase number and quality of spermatozoa in rabbit seminal liquid Part A: Effect on spermatozoon number in seminal liquid

| | 1° group of rabbits Treatment | | 2° group of rabbits Control | |
|---|---|---|---|---|
| | Before treatment | After treatment 50% D-Asp acid 50% L-Asp acid | Before treatment | After placebo treatment |
| | 305.000.000/ml seminal liquid | 355.000.000/ml seminal liquid | 310.000.000/ml seminal liquid | 308.000.000/ml seminal liquid |
| Increment | | +16.4% | | −0.7% |

Part B: Effect on spermatozoon rate

| | 1° group of rabbits Treatment | | 2° group of rabbits Control | |
|---|---|---|---|---|
| | Before treatment | After treatment | Before treatment | After placebo treatment |
| Quick motility | 37% | 47% | 37% | 36.5% |
| Increment | | +27% | | −0.2% |
| Slow motility | 26% | 26% | 27% | 28% |
| Immobile | 37% | 27% | 36% | 34% |

TABLE 9

Effect of a mixture consisting of 99.5% D-aspartic acid and 0.05% L-aspartic acid on the increase number and quality of spermatozoa in rabbit seminal liquid

|  | 1° group of rabbits Treatment | | 2° group of rabbits Control | |
| --- | --- | --- | --- | --- |
|  | Before treatment | After treatment 99.5% D-Asp acid 0.05% L-Asp acid | Before treatment | After placebo treatment |
| Part A: Effect on spermatozoon number in seminal liquid | | | | |
| Increment | 295.000.000/ml seminal liquid | 350.000.000/ml seminal liquid +18.6% | 310.000.000/ml seminal liquid | 315.000.000/ml seminal liquid +1.6% |
| Part B: Effect on spermatozoon rate | | | | |
| Quick motility | 35% | 46% | 37% | 38% |
| Increment |  | +31% |  | +2% |
| Slow motility | 26% | 26% | 27% | 28% |
| Immobile | 37% | 27% | 36% | 34% |

The results report average values obtained on a group of adult rabbits (6 month age: approximately 5 kg of body weight) before the treatment and after ingestion over 20 days of D-aspartic and L-aspartic acid mixture. The amount of the amino acid ingested by rabbit daily amounted to 570 mg of D-aspartic acid and 570 mg of L-aspartic acid.

Values reported in part A of the table refer to average number of spermatozoa/ml of seminal liquid before the drug treatment and after 20 days of treatment.

Values reported in part B of the table refer to spermatozoon motility in terms of quick, slow and immobile spermatozoa on base 100.

The increases of spermatozoon number and motility thereof in rabbits treated with D-aspartic and L-aspartic acid mixture are all significant ones. (Student T=P<0.01).

EXAMPLE 10

Study about Effects of L-Aspartic Acid on Number and Motility of the Spermatozoa on Rabbits In literature it is reported that D-aspartic acid in animal tissues including man is found in several tissues at high concentration in endocrine glands: hypophysis and testicles, is synthesised in the organism through enzyme named D-aspartate racemase having the property to synthesize D-aspartic acid by conversion of L-aspartic acid (References 21-26 and table 10).

TABLE 10

Concentration of D-Aspartate racemase in various rat tissues

| Tissues | D-Aspartate racemase (L-Asp--->D-Asp) (Enzyme unit/g tissue) |
| --- | --- |
| Testicle | 40 U/g tissue |
| Pituitary gland | 30 U/g tissue |
| Brain | 22 U/g tissue |
| Liver | 15 U/g tissue |
| Kidney | 8 U/g tissue |
| Serum | 0.2 U/g tissue |

The enzymatic activity is determined by incubation of 1 ml of reaction mixture consisting of 10 mM L-Asp 10 in borate buffer 0.M pH 8.0 at 37° C. for 60 min, with 1 ml of tissue homogenate 1:10 in borate buffer, 0.1 M pH 8.0. After incubation the amount of synthesised D-aspartic acid has been determined by HPLC (see ref. 23). 1 enzyme unit is defined as the enzyme amount suitable to convert 1 μmol of L-Asp to D-Asp under the conditions of enzymatic test.

Since the racemization is an equilibrium reaction, if by diet an amount of L-aspartic acid in ingested, a determined amount thereof will be converted in D-aspartic acid that in turn will be picked up by testicle resulting in an improved production of testosterone and quality of the seminal liquid in terms of number and motility of spermatozoa. Based on this concept we have carried out an experiment on rabbits similar to previous experiments, but administering a food containing L-aspartic acid (prepared as above described) but using L-aspartic acid instead of the D-aspartic acid. Also in this case the total amount of L-aspartic acid daily ingested by rabbit was approximately 1.1 g.

The result obtained from this study demonstrated that also by feeding the rabbits with food containing L-aspartic acid instead of D-aspartic acid, an improvement of the production, i.e. the number, of spermatozoa in the seminal liquid, not of the same grade as for D-Asp/L-Asp mixture, but still significant, was obtained. In this case increments of spermatozoon number by 14.5% and spermatozoon quick motility by 18% compared to respective semen values before the treatment have been observed (see table 11).

TABLE 11

Effect of L-aspartic acid on the increase number and quality of spermatozoa in rabbit seminal liquid

| | 1° group of rabbits Treated | | 2° group of rabbits Control | |
|---|---|---|---|---|
| | Before treatment | After treatment L-aspartic acid | Before treatment | After placebo treatment |
| Part A: Effect on spermatozoon number in seminal liquid | | | | |
| | 276.000.000/ml seminal liquid | 316.000.000/ml seminal liquid | 282.000.000/ml seminal liquid | 286.000.000/ml seminal liquid |
| Increment | | +14.5% | | +1.4% |
| Part B: Effect on spermatozoon rate | | | | |
| Quick motility | 35% | 41% | 37% | 37.5% |
| Increment | | +17% | | +1.3% |
| Slow motility | 26% | 30% | 27% | 28% |
| Immobile | 37% | 29% | 36% | 34.5% |

The results report average values obtained on a group of adult rabbits (6 month old: approximately 5 kg of body weight) before the treatment and after ingestion over 20 days of L-aspartic acid. The amount of the amino acid ingested by rabbit daily amounted to about 1.14 g. Values reported in part A of the table refer to average number of spermatozoa/ml of seminal liquid before the drug treatment and after 20 days of treatment.

Values reported in part B of the table refer to spermatozoon motility in terms of quick, slow and immobile spermatozoa on base 100.

The increases of spermatozoon number and motility thereof in rabbits treated with L-aspartic acid containing feed are all significant for Student T, $P<0.01$).

Conclusion about the Results Obtained about the Effect of the Use of the D-Aspartic Acid and the L-Aspartic Acid on the Improvement of Rabbit Seminal Liquid.

The study carried out on rabbit about the effect of L-aspartic coadjuvated D-aspartic acid demonstrated that this amino acid also the D-aspartic acid used alone or in combination with L-aspartic acid, not necessarily neutralized by sodium ions, displays an ability in improving the spermatic activity in experiment animals that is analogous to the use of sodium D-aspartate alone or in combination with sodium L-aspartate.

However, it is interesting to be point out that as when sodium D-aspartate and sodium L-aspartate are used, also the use of the D-aspartic acid in combination with L-aspartic acid in proportion of 80% D-aspartic and 20% L-aspartic, is the dose formula displaying a better effect on the spermatic activity (sees comparison of table 7, 8 and 9).

Moreover other studies carried out using also only L-aspartic acid, have demonstrated that in any case an improvement of seminal parameters has been obtained although not so high as when D-aspartic acid is used, an improvement of seminal parameters which are also significant is obtained (see table 11). The reason for this evidently results from the transformation of L-aspartic in D-aspartic acid to by racemase.

EXAMPLE 11

Study on the Man—Effects of a Combination of 80% D-Aspartic Acid and 20% L-Aspartic Acid on the Male Fertility This study has been carried out in order to know whether in addition to D-aspartate/L-aspartate, also a mixture consisting of D-aspartic acid in combination with the L-aspartic acid can result in significant improvements of the male sexual hormone increment and seminal liquid improvement, as it occurs using sodium aspartate like reported in the first part of the present patent.

The experiment has been carried out on ten 25-40 year old voluntary males selected for quality of seminal liquid being normal or almost normal.

The study involved the oral ingestion by tested subjects of a dose consisting of 1.6 g of D-aspartic acid and 0.4 g of L-aspartic acid (2.0 g total amount) after lunch and a similar dose after dinner. In terms of composition percentage the mixture consisted of 80% D-aspartic acid and 20% L-aspartic acid. Like ingestion procedure, the D-aspartic and L-aspartic acid mixture preferably was dispersed in a half filled glass containing water or fresh or stored fruit juice (orange, apple, pear, etc.), then stirred and ingested.

Before the start of the study and after 20 days of treatment in the morning from each subject blood has been collected and the concentration of LH (luteinizing hormone) and testosterone has been determined in serum obtained from said blood. Moreover, from every subject also the seminal liquid has been collected for which quick progressive motility together with total number spermatozoa/ml of sperm has been determined.

The seminal liquid has been collected by masturbation after 3-5 abstinence days. The number of the spermatozoa and progressive quick motility have been determined according to (World Health Organization) WHO guidelines using a Makler Chamber for the count (Sefi Medtstl Instrument, Haifa, Israel) and in the same place the progressive quick motility has been determined.

The result obtained from this study indicated that in 8 out of 10 treatment subjected people a serum increase of LH and testosterone hormone (specific hormones involved in the human spermatogenesis) for values before the treatment and after 20 days of treatment occurred and such increase was significant for T Student $p<0.01$. Obtained results are reported in table 12. As deduced from this table, the treatment with two daily doses of D-aspartic and L-aspartic acids resulted in an average increase of LH haematic values by 34%. From an average value of 4.1±1.2 mUI/ml in the subjects at time zero to an average value of 5.5±1.5 mUI/ml in the same subjects after 20 days of therapy, it means a 34% increase. An analogous effect has been observed for testosterone. In this case in fact, from a testosterone average value of 3.4±0.9 mUI/ml in the subjects at time zero to an average value of 5.8±1.6 mUI/ml in the same subjects after 20 days of therapy (70% increase), p<0.01 (Table 12, part A). In addition to the hormonal effect, the study evidenced that as a result of the treatment with the D-aspartic and L-aspartic acid mixture, also the spermatozoon number of the seminal liquid and progressive motility thereof are significantly increased compared to control (Table 12, parts B and C). In fact, as reported in table 12 in 9 out 10 subjects, the total number of spermatozoa in seminal liquid as a result of the treatment is significantly increased with 51.4% average increment. It is noteworthy to observe also that a subject did not respond at all to drug stimulation (sample 4 in table). Evidently very probably this results from the occurrence in the subject of a not metabolic but obstructive disorder of seminipher ducts. In addition to increased number of the spermatozoa, a significant increment of the motility thereof has been observed also. In effects the drug also induced a significant activation of the spermatozoon progressive motility. Also in this case in fact all the subjects (n. 4 excluded) displayed significant improvement of spermatozoon motility (by 67.6%) compared for the same subjects before the therapy.

TABLE 12

Effect of D-aspartic (80%) acid and L-aspartic acid (20%) on the increment of LH and testosterone in human serum and on the number and quality of the spermatozoa in human seminal liquid.

Part A
LH and testosterone concentration in serum

|  | Before Treatment | After treatment with a mixture of 80% D-Asp 80% and 20% L-Asp |
|---|---|---|
| LH (mIU/ml) | 4.1 ± 1.2 | 5.5 ± 1.5 |
| % increment |  | 34% |
| Testosterone (ng/ml) | 3.4 ± 0.9 | 5.8 ± 1.6 |
| % increment |  | 70% |

| Subjects | Before treatment | After treatment | % Increment |
|---|---|---|---|
| Part B Number of spermatozoa in seminal liquid | | | |
| 1° | $15.3 \times 10^6$ | $19.5 \times 10^6$ | 27% |
| 2° | $8.0 \times 10^6$ | $15.4 \times 10^6$ | 92% |
| 3° | $22.0 \times 10^6$ | $38.4 \times 10^6$ | 72% |
| 4° | $4.0 \times 10^6$ | $5.0 \times 10^6$ | 25% |
| 5° | $18.0 \times 10^6$ | $23.4 \times 10^6$ | 27% |
| 6° | $35.4 \times 10^6$ | $46.5 \times 10^6$ | 31% |
| 7° | $2.5 \times 10^6$ | $6.8 \times 10^6$ | 172% |
| 8° | $24.5 \times 10^6$ | $34.7 \times 10^6$ | 42% |
| 9° | $14.2 \times 10^6$ | $19.0 \times 10^6$ | 34% |
| 10° | $35.2 \times 10^6$ | $49.0 \times 10^6$ | 14% |
| % Increment | | | +53.6% ± 47.91 |
| Part C Quick progressive motility of spermatozoa | | | |
| 1° | 20% | 35% | 75% |
| 2° | 10% | 20% | 100% |
| 3° | 25% | 38% | 52% |
| 4° | 4% | 4% | 0% |
| 5° | 25% | 35% | 40% |
| 6° | 35% | 46% | 31% |
| 7° | 6% | 12% | 100% |
| 8° | 22% | 55% | 150% |
| 9° | 12% | 25% | 108% |
| 10° | 30% | 36% | 20% |
| % Increment | | | 67.6% |

Note:
Each motility value refers to liquid seminal sample of the same subject as reported in B session.
Spermatozoon motility means progressive speed as determined on the base of ocular field travelling time and is expressed as percentage of progressive quick spermatozoa of 100 observed spermatozoa.

The average increments for hormones, number and motility of the spermatozoa are all significant for T Student; $P<0.01$.

It is further pointed out that additional experiments have been carried out on other 10 people groups using the combinations of 50% D-Aspartic and 50% L-Aspartic acid and 99.5% of D-Aspartic and 0.05% L-Aspartic acid as used for the experiments on rabbits. Also on man statistically positive results as to the increase of sexual hormones and semen quality have been obtained. In this case however, the enhancement activity was lower than with combination of 80% D-Aspartic and 20% L-Aspartic acid, but however still statistically significant. Finally on the man the experiment with the use of alone L Aspartic acid instead of D-Asp/L-Asp combinations as above reported has been carried out. In this case LH and testosterone haematic hormones before and after therapy were unaltered, but the parameters of the seminal liquid were statistically improved (see table 13). In fact, as shown in said table, the number of the spermatozoa in seminal liquid of L-aspartic acid treated subjects significantly increased by 22.7% before and after D-aspartic acid treatment.

TABLE 13

Effect of L-aspartic acid on quality of human seminal liquid.

| Subjects | Before treatment | After treatment | % Increment |
|---|---|---|---|
| Parte A Number of spermatozoa in seminal liquid | | | |
| 1° | $16 \times 10^6$ | $18 \times 10^6$ | 12% |
| 2° | $5 \times 10^6$ | $8 \times 10^6$ | 26% |
| 3° | $25 \times 10^6$ | $35 \times 10^6$ | 40% |
| 4° | $5 \times 10^6$ | $6 \times 10^6$ | 20% |
| 5° | $15.0 \times 10^6$ | $20 \times 10^6$ | 33% |
| 6° | $30 \times 10^6$ | $41 \times 10^6$ | 36% |
| 7° | $2 \times 10^6$ | $3 \times 10^6$ | 15% |
| 8° | $30 \times 10^6$ | $34 \times 10^6$ | 13% |
| 9° | $45 \times 10^6$ | $51 \times 10^6$ | 13% |
| 10° | $21 \times 10^6$ | $25 \times 10^6$ | 19% |
| % Increment | | | +22.7% ± 10.41 |
| Part B Progressive quick motility of spermatozoa | | | |
| 1° | 18% | 25% | 38% |
| 2° | 15% | 19% | 26% |
| 3° | 24% | 35% | 45% |
| 4° | 12% | 18% | 50% |
| 5° | 32% | 40% | 25 |
| 6° | 35% | 45% | 28% |
| 7° | 16% | 22% | 37% |

TABLE 13-continued

Effect of L-aspartic acid on quality of human seminal liquid.

| Subjects | Before treatment | After treatment | % Increment |
|---|---|---|---|
| 8° | 19% | 27% | 42% |
| 9° | 25% | 35% | 40% |
| 10° | 31% | 39% | 25% |
| % Increment: Average ± SD | | | +35.6% ± 9.05 |

Note:
Each motility value refers to liquid seminal sample of the same subject as reported in B session.
Spermatozoon motility means progressive speed as determined on the base of ocular field travelling time and is expressed as percentage of progressive quick spermatozoa of 100 observed spermatozoa.

The average increments for hormones, number and motility of the spermatozoa are all significant for T Student; P<0.01.

Preparation of Supplement and Combination with Excipients

As to the ingestion route of the supplement it is to pointed out that D-aspartic and L-aspartic are both hardly soluble aqueous solvents. Therefore 2 grams of suggested dose (2 grams 2 times daily, see above) mixed with water or fruit juice half filled glass are not completely dissolved. However also if the dose is ingested as semi insoluble mixture, in the stomach is diluted with copious liquid and gastric juices thus soluble and intestine absorbable. The expedient to use the supplement as two doses, each containing 2 g, at two main meals results in a better effectiveness than the use of daily dose.

As to the opportunity for the addition of excipients (vitamins, Q-10 coenzyme, mineral salts, etc.) to said drug during the commercial preparation, the addition of suitable dose of the following supplements could be useful for the drug enhancement in terms of efficiency: zinc oxide in amount of 5-10 mg/drug dose (zinc occurs in seminal liquid and it is thought that positively affects the testosterone regulation within the prostate). Q-10 coenzyme in amount of 10-20 mg/drug dose (Q10 coenzyme is an important antioxidant agent and protect the cells against free radicals) and other excipients useful in order to improve drug acceptability as for example Vitamins, folic acid etc. in amounts as accepted for food use.

BIBLIOGRAPHY (1) D'Aniello A. and Giuditta A. Identification of D-aspartic acid in the brain of *Octopus vulgaris*. *J. of Neurochemistry*. 29, 1053-1057, 1977.
(2) D'Aniello A. and Giuditta A. Presence of D-aspartate in squid axoplasm and in other regions of the cephalopod nervous system. *J. of Neurochemistry*. 31, 1107-1108, 1978.
(3) D'Aniello A. Di Cosmo A., Di Cristo C., and Fisher G. D-aspartate in the male and female reproductive system of *Octopus vulgaris Lam. General and Comparative Endocrinology*. 100, 69-72, 1995.
(4) D'Aniello A., Spinelli P., De Simone A., D'Aniello S., Branno B., Aniello F., Fisher G., Di Fiore MM. and Rastogi KK. Occurrence and neuroendocrine role of D-aspartic acid and NMDA in *Ciona Intestinalis*. *FEBS letters*. 552, 193-198, 2003.
(5) Di Fiore MM., Assisi, L., Botte, V. and D'Aniello A. D-Aspartic acid is implicated in the control of testosterone production by the vertebrate gonad. Studies on the female green frog *Rana esculenta*. *J. of Endocrinology*. 156, 199-207, 1998.
(6) D'Aniello A., Nardi G., De Santis A., Vetere A., Di Cosmo A., Marchelli R., Dossena A., and Fisher G. Free L-amino acids and D-aspartate content in the nervous system of cephalopoda. A comparative study. *Comp. Biochem. Physiol.* 112, 661-666, 1995.
(7) Raucci F., Santillo A., D'Aniello A., Chieffi P., Chieffi G. Baccari. D-Aspartate modulates trascriptional activity in harderian gland of frog, *Rana esculenta*: Morphological and Molecular Evidence. *J. of Cell. Physiol.:* 204, 445-454, 2005.
(8) Assisi L., Botte V., D'Aniello A. and Di Fiore MM. Enhancement of aromatase activity by D-aspartic acid in the ovary of lizard *Podarcis sicula*. *Reproduction*. 121, 803-808, 2001.
(9) Neidle A., and Dunlop DS. Developmental changes of free D-aspartic acid in the chicken embryo and in the neonatal rat. *Life Science*. 46, 1517-1522, 1990.
(10) D'Aniello A., D'Onofrio G., Pishetola M., D'Aniello G., Vetere A., Petrucelli L. and Fisher G. Biological role of D-amino acid oxidase and D-aspartate oxidase. Effects of D-amino acids. *J. Biol. Chem.:* 268, 26941-26949, 1993.
(11) Hashimoto A., Nishikawa T., Oka T., Hayashi T and Takahashi K. Widespread distribution of free D-aspartate in rat periphery. *FEBS Letters*. 331, 4-8, 1993.
(12) Boni R., Santillo R., Macchia G., Spinelli P., Ferrandino G. and D'Aniello A. D-aspartate and reproductive activity in sheep. *Theriogenology*. 65, 1265-1278, 2006.
(13) Dunlop DS., Neidle A., McHale D., Dunlop DM. and Lajtha A. The presence of free D-Aspartic acid in rodents and man. *Biochem. Biophys. Res. Comm*. 142, 27-32, 1986.
(14) Fisher GH., D'Aniello A., Vetere A., Padula L., Cusano C., Man EH. Free D-aspartate and D-alanine in normal and Alzheimer brain. *Brain Res. Bull.:* 26, 983-985, 1991.
(15) Hashimoto A., Kumashiro S., Nishikawa T., Oka T., Takahashi K., Mito T., Takashima S., Doi N., Mizutani Y., Kaneco T. and Ootomo E. Embryonic development and postnatal changes in free D-aspartate and D-serine in the human prefrontal cortex. *J. Neurochem.:* 61, 348-351, 1993.
(16) D'Aniello A. D-Aspartic acid: An endogenous amino acid with an important neuroendocrine role. *Brain. Research Review.* 53, 215-234, 2006.
(17) D'Aniello A., Di Cosmo A., Di Cristo C., Annunziato L., Petrucelli L., and Fisher GH. Involvement of D-aspartic acid in the synthesis of testosterone in rat testes. *Life Science*. 59, 97-104, 1996.
(18) D'Aniello A., Di Fiore MM., Fisher GH., Milone A., Seleni A., D'Aniello S., Perna A., and Ingrosso D. Occurrence of D-Aspartic acid and N-methyl-D-aspartic acid in rat neuroendocrine tissues and their role in the modulation of luteinizing hormone and growth hormone release. *FASEB J*. 14, 699-714, 2000.
(19) D'Aniello G., Tolino A., D'Aniello A., Fisher GH. and Di Fiore MM. The role of the D-aspartic acid and N-methyl-D-aspartic acid in the regulation of prolactin release. *Endocrinology*. 141, 3862-3870, 2000.
(20) D'Aniello G., Ronsini S., Guida F., Spinelli P. and D'Aniello A. Occurrence of D-aspartic acid in human seminal plasma and spermatozoa: Possible role in reproduction. *Fertility and Sterility*. 84, 1444-1449, 2005.
(21) D'Aniello S, Spinelli P., Ferrandino G., Peterson G., Tsesarskia T., Fisher G. and D'Aniello A. Cephalopod

(22) Shibata, K., Watanabe, T., Yoshikawa, H., Abe, K., Takahashi, S., Kera, Y., and Yamada, R. H. (2003). Purification and characterization of aspartate racemase from the bivalve mollusk *Scapharca broughtonii*. Comp. Biochem. Phys. B. 134, 307-314.

(23) D'Aniello, S., Spinelli, P., Ferrandino, G., Peterson, K., Tsesarskaja, M., Fisher, G., and D'Aniello, A. (2005). Cephalopod vision involves dicarboxylic amino acids: D-aspartate, L-aspartate and L-glutamate. Biochem. J. 386, 331-340.

(24) Spinelli, P., Brown, E., Ferrandino, G., Branno, M., Montarolo, P. G., Rastogi, R. K., D'Aniello, B., Chieffi, G., Fisher, G., and D'Aniello, A. (2006). D-Aspartic acid in the nervous system of *Aplysia limacina*: Possible role in neurotransmission. J. Cell. Physiol. 206, 672-681.

(25) Wolosker, H. A., D'Aniello, A., and Snyder, S. H. (2000). D-aspartate disposition in neuronal and endocrine tissues: ontogeny, biosynthesis and release. Neuroscience 100, 183-189.

(26) Topo E, Soricelli A, D'Aniello A, Ronsini S, D'Aniello G. The role and molecular mechanism of D-aspartic acid in the release and synthesis of LH and testosterone in humans and rats. Reprod. Biol. Endocrinol. 7, 120-131 (2009).

We claim:

1. An oral composition for use in the treatment of male infertility comprising:
    a combination of D-aspartic acid or one or more alkaline or alkaline earth metal salts thereof and L-aspartic acid or one or more alkaline or alkaline earth metal salts thereof, and
    one or more pharmaceutically acceptable excipient(s) and/or one or more coadjuvant(s),
    wherein the concentration of D-aspartic acid or salts thereof is from 80% to 99.5% and the concentration of L-aspartic acid or salts thereof is from 0.5% to 20%, said percentages based on total weight of D-aspartic and L-aspartic acids or salts thereof in said composition.

2. The oral composition according to claim 1, wherein said composition consists of:
    a combination of D-aspartic acid or one or more alkaline or alkaline earth metal salts thereof and L-aspartic acid or one or more alkaline or alkaline earth metal salts thereof, and
    one or more pharmaceutically acceptable excipient(s) and/or a one or more coadjuvant(s),
    wherein the concentration of D-aspartic acid or salts thereof is from 80% to 99.5% and the concentration of L-aspartic acid or salts thereof is from 0.5% to 20%, said percentages based on total weight of D-aspartic and L-aspartic acids or salts thereof in said composition.

3. The oral composition according to claim 1, wherein said one or more coadjuvants coadjuvant(s) are selected from the group consisting of amino acids, ketoacids, vitamins, minerals, reproductive function stimulating hormones, kallikrein, antibiotics, anti-inflammatory agents, antiandrogens, androgens, pentoxifilline, gonadotropine, gonadotropine releasing hormone (GnRH), adrenergic stimulators, dietetic supplements, anti-oxidants, and ketoacids.

4. The oral composition according to claim 3, wherein said amino acids are selected from the group consisting of alanine, arginine, carnitine, cysteine, glutamine, glycine, leucine, lysine, isoleucine, methionine, ornithine, phenylalanine, threonine, tryptophan, valine, and serine.

5. The oral composition according to claim 3, wherein said vitamins are selected from the group consisting of vitamin A, C, D3, E, K, B1, B2, B6, B12, PP, biotin (H), folic acid, lipoic acid and Q10 coenzyme.

6. The oral composition according to claim 3, wherein said minerals are selected from the group consisting of magnesium, potassium, zinc, manganese, molybdenum, chromium, selenium, calcium, iron, copper, iodine, phosphorus, and fluorine.

7. The oral composition according to claim 5, wherein the concentrations of vitamins are: vitamin A from 0.0048% to 0.024%, vitamin C from 0.36% to 3.6%, vitamin D3 from 0.00003% to 0.00015%, vitamin E from 0.06% to 0.6%, vitamin K from 0.00042% to 0.0021%, vitamin B1 from 0.0084 to 0.042%, vitamin B2 from 0.0096% to 0.048%, vitamin B6 from 0.012% to 0.06%, vitamin B12 from $6 \times 10^{-6}\%$ to $3 \times 10^{-5}\%$, vitamin PP from 0.108% to 0.54%, biotin from 0.0009% to $4.4 \times 10^{-5}\%$, folic acid from 0.0012% to 0.006%, said percentages being % weight based on total composition weight.

8. The oral composition according to claim 6, wherein the concentrations of minerals are: magnesium from 3.2% to 9%, potassium from 0.4% to 4%, zinc from 0.09% to 0.45%, manganese from 0.02% to 0.07%, molybdenum, chromium or selenium from 0.0003% to 0.002%, calcium pantothenate from 0.04% to 0.15%, iron from 0.084% to 0.021%, copper from 0.02% to 0.1%, iodine from 0.0009% to 0.0045%, phosphorus from 2.5% to 20%, fluorine from 0.005% to 0.02%, calcium from 3.24% to 16.2%, said percentages being % weight based on total composition weight.

9. The oral composition according to claim 1, wherein the concentrations of amino acids in addition to D-aspartic and L-aspartic acids is from 0.6% weight to 10% weight based on total composition weight.

10. The oral composition according to claim 1, wherein said composition further comprises folic acid, vitamin B6, vitamin B12, potassium sorbate and sodium benzoate.

11. The oral composition according to claim 10, wherein said folic acid concentration is from 0.002% to 0.006%, said Vitamin B6 concentration is from 0.02% to 0.06%, said Vitamin B12 concentration is from $1 \times 10^{-5}\%$ to $3 \times 10^{-5}\%$, said potassium sorbate concentration is from 0.002 to 0.008%, and said sodium benzoate concentration is from 0.002 to 0.008%.

* * * * *

UNITED STATES PATENT AND TRADEMARK OFFICE
CERTIFICATE OF CORRECTION

PATENT NO. : 11,524,031 B2
APPLICATION NO. : 16/504372
DATED : December 13, 2022
INVENTOR(S) : Salvatore D'Aniello and Enrico D'Aniello Page 1 of 1

It is certified that error appears in the above-identified patent and that said Letters Patent is hereby corrected as shown below:

In the Specification

Column 6,
Line 30, "to 0.070," should read --to 0.07%,--.

Column 25,
Lines 22-23, "group of adult rabbits" should read --group of 10 adult rabbits--.

In the Claims

Column 31,
Line 58, "one or more coadjuvants coadjuvant(s) are" should read --one or more coadjuvant(s) are--.

Signed and Sealed this
Fifth Day of September, 2023

Katherine Kelly Vidal
*Director of the United States Patent and Trademark Office*